(12) United States Patent
Nikolic et al.

(10) Patent No.: US 6,436,052 B1
(45) Date of Patent: Aug. 20, 2002

(54) METHOD AND SYSTEM FOR SENSING ACTIVITY AND MEASURING WORK PERFORMED BY AN INDIVIDUAL

(75) Inventors: Serjan D. Nikolic, San Francisco;
Audie W. Hickey, Union City;
Kenneth P. Aron, Burlingame, all of CA (US)

(73) Assignee: Telecom Medical, Inc., Cupertino, CA (US)

( * ) Notice: Subject to any disclaimer, the term of this patent is extended or adjusted under 35 U.S.C. 154(b) by 0 days.

(21) Appl. No.: 09/415,950

(22) Filed: Oct. 8, 1999

Related U.S. Application Data

(63) Continuation-in-part of application No. 09/050,332, filed on Mar. 30, 1998, now abandoned.
(60) Provisional application No. 60/042,159, filed on Mar. 31, 1997.

(51) Int. Cl.$^7$ ................................................. A61B 5/08
(52) U.S. Cl. ........................ 600/529; 600/300; 600/481; 600/484
(58) Field of Search .............................. 600/300–301, 600/481, 483–484, 587, 529, 532

(56) References Cited

U.S. PATENT DOCUMENTS 6,016,443 A * 1/2000 Ekwall et al. .............. 600/519
6,135,951 A * 10/2000 Richardson et al. ........ 600/300
6,241,684 B1 * 6/2001 Amano et al. .............. 600/531
6,275,727 B1 * 8/2001 Hopper et al. .............. 600/513

* cited by examiner

Primary Examiner—Kevin Shaver
Assistant Examiner—Patricia Mallari
(74) Attorney, Agent, or Firm—Jonathan W. Richards

(57) ABSTRACT

Systems and methods providing for the determination of an individual's rate of oxygen consumption, in order to determine the amount of work that is performed by the individual's body. A heart monitor measures the heart rate of the individual and an accelerometer measures the acceleration of the body. The heart rate and acceleration outputs are stored locally on a storage device. The outputs can be downloaded to a local base station, that in turn transmits the outputs to a central clearinghouse. The clearinghouse receives and stores the output on a central mass storage device. At the clearinghouse the raw data is processed into a usable form and the rate of oxygen consumption is mathematically determined in order to determine the amount of work that is performed on the individual's body. The processing includes separating the static and dynamic acceleration components, calculating the dynamic acceleration magnitude, calculating the maximum change in acceleration, filtering the dynamic acceleration component, and graphing the resulting filtered dynamic acceleration with respect to time.

17 Claims, 16 Drawing Sheets

METHOD AND SYSTEM FOR SENSING ACTIVITY AND MEASURING WORK PERFORMED BY AN INDIVIDUAL

RELATED APPLICATIONS

This application is a continuation-in-part of U.S. application Ser. No. 09/050,332, filed Mar. 30, 1998, abandoned and also claims the benefit of priority of U.S. Provisional Application No. 60/042,159, filed Mar. 31, 1997.

BACKGROUND OF THE INVENTION

1. The Field of the Invention

The present invention pertains to the field of physiological monitoring. More particularly, the present invention relates to a method and system for determining an individual's rate of oxygen consumption in order to measure the amount of work performed by the individual's body.

2. The Prior State-of-the-Art

Human health can be determined and treated upon analyzing specific physiological characteristics of a human body. One such physiological characteristic, the rate for which the human body consumes oxygen, provides one of the best measurements for analysis of work performed by the human body. Within the body, the cardiovascular system delivers oxygen to the muscles for the use in burning various fuels such as carbohydrates and fats, thereby yielding energy. This rate of oxygen consumption is commonly known as VO2.

Traditionally, an individual's VO2 has been obtained by comparing the individual's inhaled air volume from his/her exhaled air volume. This comparison is performed on air volumes measured while the individual, being connected to a gas analyzer, runs on a treadmill in a specialized testing facility. The inhaled and exhaled air volumes pass through the gas analyzer for a determination of the oxygen concentration of each air volume. The difference in the volumes of air is said to be the amount of oxygen that the muscles have consumed to burn fuel.

While the rate of oxygen consumption has become valuable information for determining an individual's fitness, the traditional method for measuring VO2 has been very confining. Since inhaled and exhaled air volumes are required to pass through a gas analyzer, the testing is confined to a specialized testing facility. As such, the types of physical activities performed during a traditional VO2 test are limited to activities that can be performed inside a laboratory, such as running on a treadmill, and therefore do not allow the individual to perform his/her usual physical activities under normal conditions.

The traditional method for testing VO2 is further confining because of the requirement of a mouthpiece used to connect the individual's body to the gas analyzer. A mouthpiece covering the individual's mouth and/or nose creates an artificial condition since the individual would not use the mouthpiece under normal conditions and is not accustomed to exerting himself/herself with the use of the mouthpiece. Furthermore, if the mouthpiece does not allow for the passage of air through both the mouth and the nose, the traditional method further confines the individual by requiring the use of only one air passage. Moreover, if the seal on the mouthpiece is broken, oxygen will be allowed to pass through the broken seal, thereby generating erroneous results.

It would therefore be an advancement in the art to determine an individual's rate of oxygen consumption while he/she undergoes physical activity in a location where that physical activity would normally take place, rather than in a specialized testing facility. Further, it would be highly desirable that an individual's rate of oxygen consumption be measured while that individual is exerting the type of physical activity that he/she normally undergoes. It would also be desirable for the method of determining the rate of oxygen consumption to allow for the individual to have free movement rather than being connected to laboratory equipment. It also would be desirable for the rate of oxygen consumption to be determined without the use of a mouthpiece that may cause erroneous results.

SUMMARY AND OBJECTS OF THE INVENTION

The present invention relates to methods and systems for determining an individual's rate of oxygen consumption in order to measure the amount of work performed by the individual's body. A heart monitor is used to measure the heart rate, and an accelerometer is used to measure acceleration. The heart rate and acceleration outputs are stored in a local storage device and can be downloaded to a local base station. After the base station receives the outputs, the heart monitor and accelerometer are available to take more measurements. The base station, meanwhile, is available to upload the outputs to a central clearinghouse for processing.

At the clearinghouse the outputs are processed into a usable form to determine the individual's rate of oxygen consumption, also known as VO2, in order to measure the amount of work that is performed by the individual's body. More specifically, the acceleration outputs are collected, and mathematical algorithms are employed, to initially convert the outputs into motion information and then into activity information. The heart rate and activity information are then graphed on the same time base for determining their relationship.

As explained above, the present invention relates to methods and systems for determining an individual's rate of oxygen consumption in order to measure the amount of work performed by the individual's body. The methods and systems of the invention allow for the heart rate and acceleration measurements to be taken at a location where the activity would normally take place, such as in a gymnasium or a swimming pool, on a track, a court or a field, or at home. Furthermore, the methods and systems allow for the activity to take place under normal conditions, as will be described in detail below.

Additional objects and advantages of the invention will be set forth in the description that follows, and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof that are illustrated in the appended claims. Understanding that these drawings depict only typical embodiments of the invention and are not therefore to be considered to be limiting of its scope, the invention will be described and explained with additional specificity and detail through the use of the accompanying drawings in which:

DETAILED DESCRIPTION OF THE PREFERRED EMBODIMENTS

Figure 1:
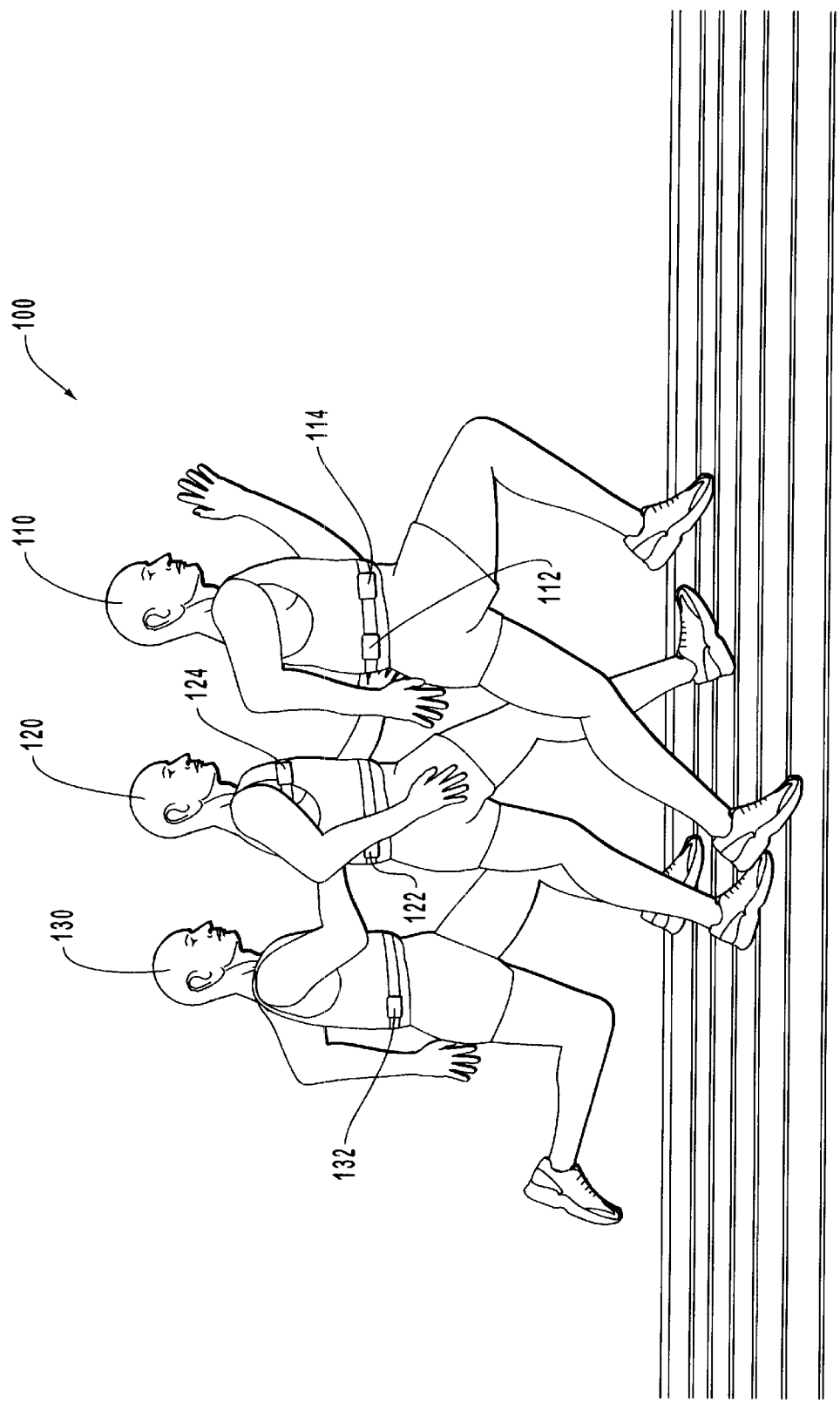
FIG. 1 is an example of a suitable operating environment for the present invention.

The present invention contemplates both methods and systems for determining an individual's rate of oxygen consumption, also known as VO2, in order to measure the amount of work performed by the individual's body. In accordance with the present invention, an individual's VO2 is able to be determined while he/she undergoes physical activity in a location where the physical activity would normally take place, such as on a track, a field, a court, in a gymnasium, a swimming pool, or at home. A heart monitor and an accelerometer respectively measure the individual's heart rate and acceleration while he/she undergoes physical activity. The measurements are processed to determine the VO2 for that individual's body. The processing is used to determine the relationship between the individual's activity and heart rate.

The present invention is described below by using diagrams to illustrate either the structure or processing of embodiments used to implement the methods and systems for determining VO2, in order to measure the amount of work that is performed by an individual's body. Using the diagrams in this manner to describe the present invention should not be construed as limiting its scope.

The invention will be described below in reference to measuring the amount of work that is performed by an individual's body through determining the individual's VO2 while he/she undergoes physical activity under normal conditions. In this context, both in the description and in the claims, "physical activity" is used to refer to any type of exercise, exertion or movement that the individual undergoes during the period of time that measurements are taken. "Physical activity" further includes normal daily activities, whether at nominal rest or in a period of physical exertion. Examples of physical activity include running, walking, jogging, jumping, swimming, biking, pushing, pulling, or any other type of physical movement that a human body can undergo.

In the description and in the claims, "normal conditions" is used to refer to the surroundings, circumstances and manners under which a particular individual usually undergoes a physical activity. Further, "normal conditions" is specific to the individual of whom the measurements are taken. By way of example, "normal conditions" includes performing physical activity on a track, court, field, or a street, on grass, concrete, or carpet, in a gymnasium or swimming pool, at home or at work, or any other environment or location where the individual usually undergoes physical activity. Furthermore, "normal conditions" refers to limiting the amount of artificial conditions so that the artificial conditions do not affect the physical activity being performed by the individual.

Under the present invention, measurements are taken to yield a determination of the amount of work performed. Implementation of the present invention applies not only to sports and athletics, but also to fitness generally. In other words, the present invention can be applied not only for determining the VO2 or work of a professional athlete while that athlete is performing his/her profession, but also to every day men, women and children undergoing their own recreation and daily routines, whether they are sporting events, exercise routines, work routines, routines for upkeep of a home and/or a yard, routines for taking care of children, and so forth.

The invention will be described below in reference to a monitor for measuring data and/or obtaining information. In this context, "monitor" or "monitoring device" is used to refer to any type of device, apparatus, or mechanism that can be utilized for measuring or obtaining data and/or information. Such means for measuring can include any device, apparatus, or mechanism that is external, attached to, or embedded within an individual's body. As such, "monitor" or "monitoring device" includes an external sensor, an internal sensor, an adhesive patch, a radar gun, or any other means whereby information can be obtained or measured.

Now referring to FIG. 1, a suitable environment is illustrated, by way of example, in which the present invention may be implemented. While the present invention can be implemented upon any physical activity performed under normal conditions, as explained above, FIG. 1 illustrates embodiments of the present invention being implemented while a race is run on a track, depicted generally as 100. As will be explained below, monitoring devices are employed to obtain information from each of the three individuals running the race.

Individual 110 and the corresponding monitoring devices depict an embodiment of the present invention. A belt system is attached around the waist of individual 110 and includes activity monitor 112 for measuring activity and heart monitor 114 for measuring the heart rate. In one embodiment, activity monitor 112 includes a monitor, such as an accelerometer, for measuring activity or acceleration. Further, in one embodiment, activity monitor 112 also includes a local storage device for storing the acceleration output information measured while heart monitor 114 also includes a local storage device for storing the heart rate output information. In yet another embodiment, activity monitor 112 and heart monitor 114 communicate, such that one of the monitors transmits the measured information to the other monitor and all of the heart rate and acceleration outputs obtained from individual 110 are stored on a local storage device in one monitor. By way of example, one embodiment allows for the heart rate and acceleration outputs to be stored locally on activity monitor 112. The means for communication between activity monitor 112 and heart monitor 114 can include a wire, an RF transmission, an IR link, or any other means capable of transmitting a signal.

Another embodiment is illustrated by individual 120 and the corresponding monitoring devices. A belt system containing activity monitor 122 wraps around the waist of individual 120 while a belt system containing heart monitor 124 wraps around the chest area. In a similar manner as explained above, activity monitor 122 can include a monitor, such as an accelerometer, for measuring activity or acceleration and heart monitor 124 measures the heart rate. Further, in one embodiment, activity monitor 122 includes a local storage device for storing the acceleration output while heart monitor 124 includes a local storage device for storing the heart rate output. In another embodiment, activity monitor 122 and heart monitor 124 communicate, such that one of the monitors transmits the measured output information to the other monitor and all of the output information is stored locally in one monitor. By way of example, one embodiment allows for the heart rate information and acceleration information to be stored locally on activity monitor 122. The means for communication between activity monitor 122 and heart monitor 124 can similarly include a wire, an RF transmission, an IR link, or any other means capable of transmitting a signal.

Another embodiment is illustrated using individual 130 and the corresponding monitoring device. In one embodiment, monitor 132 includes a monitor, such as an accelerometer, for measuring activity or acceleration and a local storage device for storing the heart rate and acceleration output information of individual 130. In another embodiment, monitor 132 also includes a heart monitor for measuring the heart rate.

Other embodiments of the present invention provide for multiple activity monitors, or accelerometers, and/or heart monitors for obtaining multiple outputs. By way of example, one embodiment includes two accelerometers, one being located at the lower back and the other being located on the side. Further, other embodiments of the present invention only provide for one or more activity monitors. By way of example, an embodiment includes at least one activity monitor, or accelerometer, and no heart monitor.

While FIG. 1 illustrates a monitoring device located at the lower back of individuals 110, 120, and 130, embodiments of the present invention allow for the monitoring devices to be located at various areas of the body. A heart monitor requires that a pulse be measured in order for heart rate information to be obtained, and as such the monitor can be placed on various locations of the body so long as the pulse can be measured. And since physical movement takes place in different areas of the body, depending on the activity performed, the accelerometer can also be located at various areas of the body in order to obtain optimal acceleration measurements for the activity performed. Furthermore, the locations of the monitoring devices can change to provide free movement by the individual undergoing the physical activity. In FIG. 1, individuals 110, 120, and 130 are free to move as they normally would in running the race under normal conditions. The free movement is available because all of the instrumentation is placed on the body and the instrumentation does not require the connection to an external analyzer or device. Therefore, the instrumentation does not hinder the individual's movement.

In one embodiment, the output information is transmitted or downloaded to a base station, as will be further explained below. The base station can be coupled to one or both of the monitors to receive all of the measured output information. The means for communication with the base station can include an IR link, an RF link, a wire, a fiber-optic cable, or any other means for transmitting information. In one embodiment, the base station periodically sends a signal to determine if a monitoring device is within range of the base station and is available to download the output information to the base station. In one embodiment, the user is notified of a proper connection or alternatively of an improper connection by, for example, a visual or audible notification, such as the illumination of a light or sounding of a tone. Also in an embodiment, the base station transmits or uploads the output information to a remote processing facility, such as a central clearinghouse, as will be further explained below.

Figure 2:
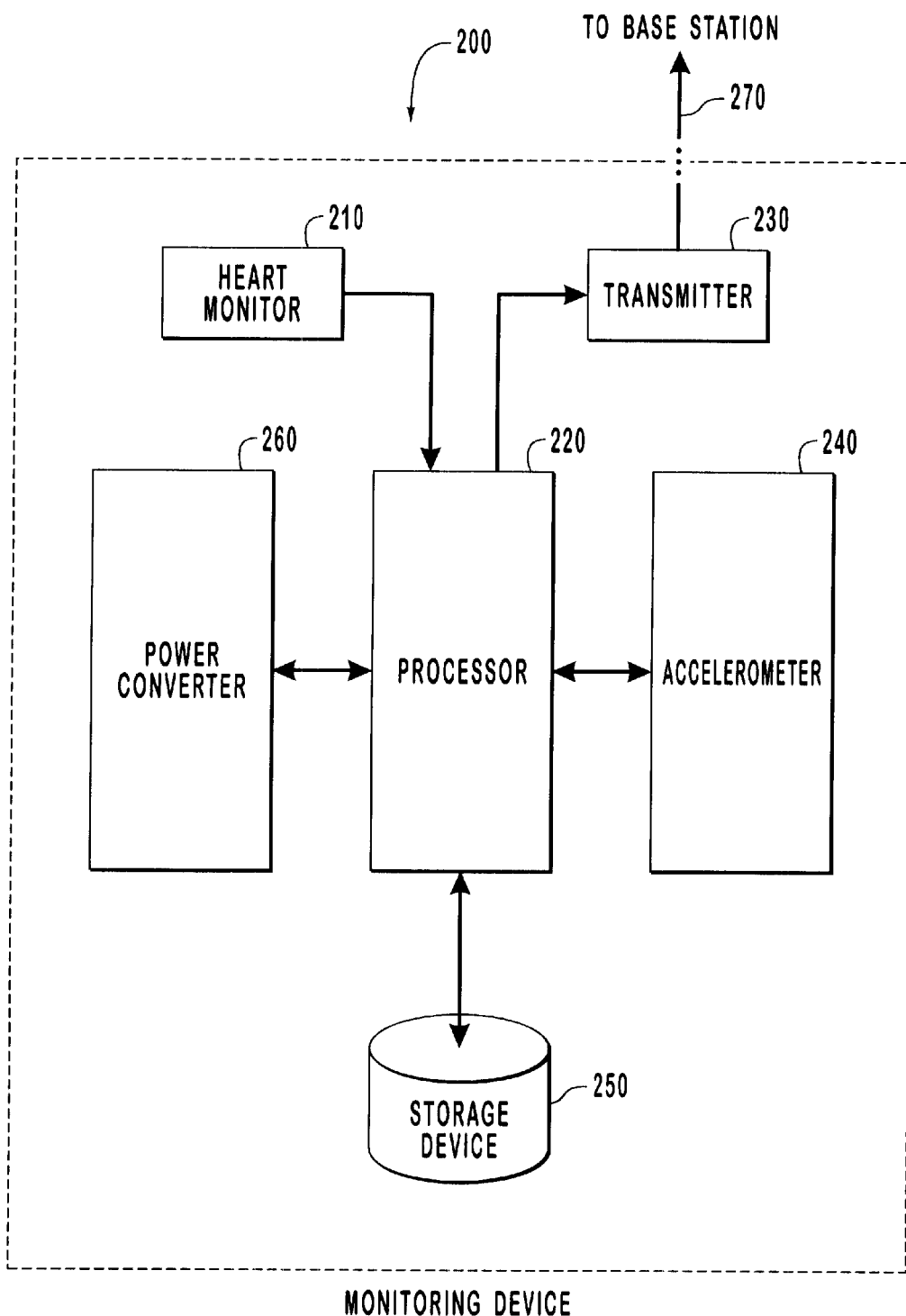
FIG. 2 is a schematic drawing of a monitoring device.

Referring now to FIG. 2, a monitoring device is illustrated generally as monitoring device 200 and is similar to one embodiment of monitor 132, of FIG. 1, in that the heart monitor and accelerometer are included into one monitoring device. Heart monitor 210 measures the heart rate, and can be any type of device capable of obtaining heart rate information from an individual. Processor 220 saves the heart rate output information on storage device 250, which can comprise any medium that can be used to store data, such as an optical or magnetic storage device. Monitoring device 200 can also include power converter 260 to maximize space and increase the power available.

Monitoring device 200 also includes accelerometer 240 for measuring acceleration. More specifically, accelerometer 240 provides simultaneous measurements on one, two, or three axes: vertical, longitudinal and lateral. Further, accelerometer 240 responds to force along each axis. Through mathematical manipulation of the measurements obtained from accelerometer 240, motion information can be obtained that can be converted into activity information, as will be further explained below. The accelerometer output is stored on mass storage 250. After the acceleration and heart rate outputs are obtained, monitoring device 200 can be coupled to a base station via link 270 so that the heart rate and acceleration information located on mass storage 250 can be transmitted or downloaded to a mass storage device within the base station through the use of transmitter 230, as shall be further explained below.

In one embodiment, processor 220 is a PIC processor that requires small amounts of energy. However, in order to have processor 220 be a PIC processor, one embodiment requires that the amount of data measured be a power of two in order to optimize the manipulation of data. Therefore, in order to ensure that the number of data samples is a power of two, in one embodiment the sampling rate is approximately 59 milliseconds. As such, when averages are taken, as will be explained below, the number of data samples becomes a power of two.

As mentioned above, once the heart rate and acceleration outputs are obtained from heart monitor 210 and accelerometer 240, the output information can be processed at several locations. By way of example, in one embodiment, the heart rate and acceleration outputs are locally stored in monitoring device 200 and are locally processed. In another embodiment, the heart rate and acceleration outputs are stored on a storage device in a base station and the output information is available for processing at the base station. In another embodiment, the heart rate and acceleration output information are uploaded to and stored at a central clearinghouse for processing at the central clearinghouse.

Figure 3:
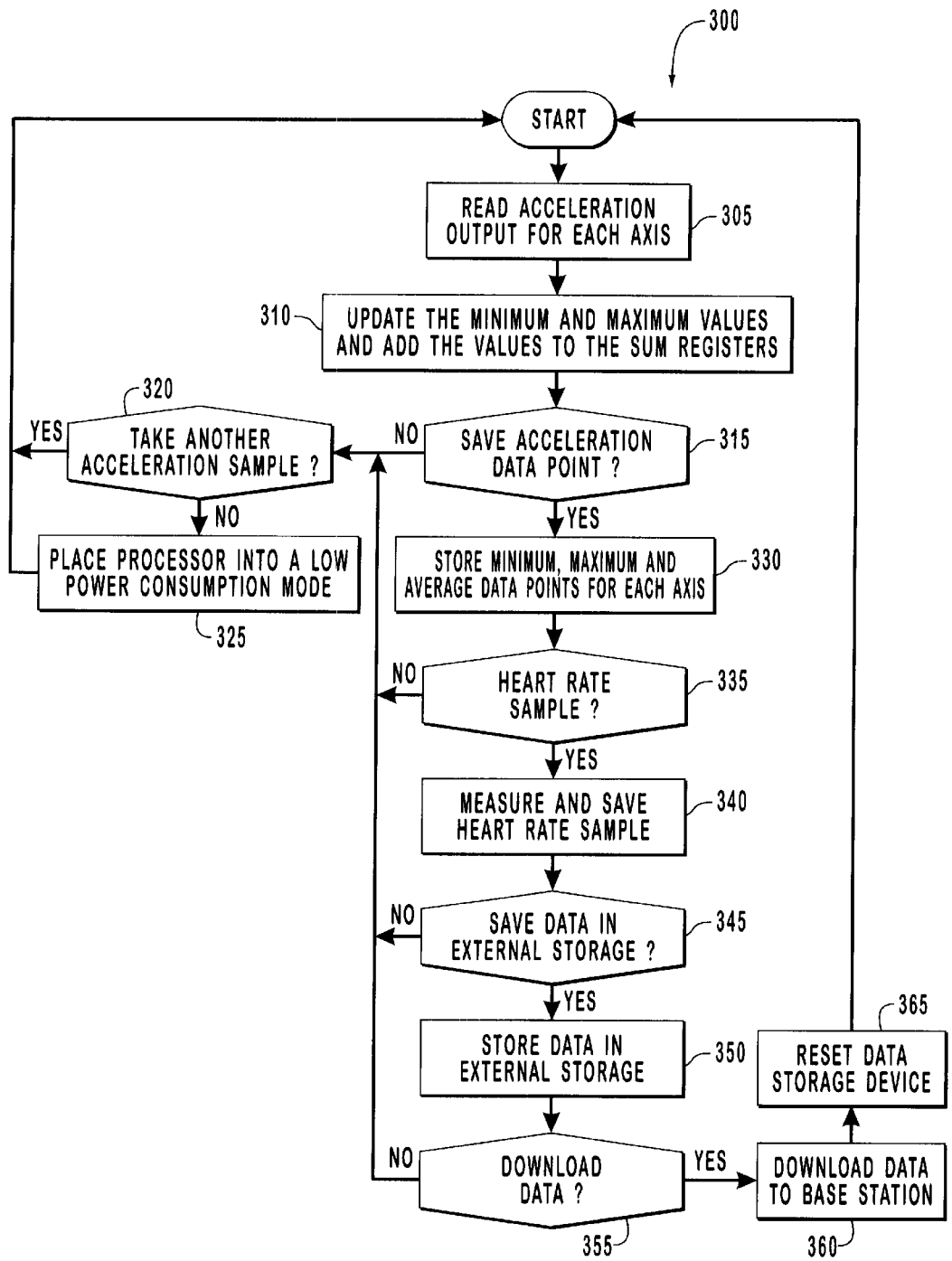
FIG. 3 is a flow chart illustrating a method for obtaining and downloading heart rate and acceleration measurements, according to one embodiment of the present invention.

Referring now to FIG. 3, a flow chart is provided to illustrate an embodiment of the overall system logic of monitoring device 200. In step 305, the output of the accelerometer or activity monitor is obtained. The acceleration output information can be read as an analog voltage, or can be read digitally using a Pulse Width Modulated (PWM) output. In the embodiment of FIG. 3, the acceleration output information is read as an analog voltage and includes acceleration information from two orthogonal axes.

In step 310 the acceleration output or data for each axis is added to a cumulative sum for the corresponding axis. The acceleration data is compared to the minimum and maximum values of the information obtained in step 305. If the data point is a new minimum or maximum, the data point is saved on storage device 250 of FIG. 2. By way of example, this can be done by employing a look-up table in ROM and taking the magnitude of the resultant values, or alternatively by designating one axis to determine the maximum and minimum data points.

Decision block 315 inquires as to whether or not it is time to save an acceleration data point. In one embodiment, the time between saving data points is approximately 1.875 seconds. That time interval can be shorter, longer, or adaptive depending on the activity being monitored. If it is not yet time to save an acceleration data point, decision block 320 inquires as to whether another acceleration sample should be taken. In one embodiment, the time between samples is 29.3 milliseconds. If another acceleration sample should be taken, the program execution branches back to step 305. If it is not time to take another acceleration sample, step 325 places processor 220 of FIG. 2 into a low power consumption mode of operation until the time that their next sample is to be taken. The time of the low power operation mode is predetermined and upon resuming program execution the program branches to step 305 above.

From above, if decision block 315 determines that it is time to save an acceleration data point, the program execution branches to step 330 where the acceleration data is stored in RAM. In one embodiment, the average acceleration data is calculated by dividing the cumulative values obtained in step 310 by the number of sample points. And, by way of example, in the embodiment where the time between saving data points is approximately 1.875 seconds and the time between samples is 29 milliseconds, the number of sample points would be 64.

The acceleration data point consists of 6 bytes when measuring acceleration information from two orthogonal axes. A first byte is used for the minimum acceleration point of a first axis. A second byte is used for a minimum acceleration point of a second axis. A third byte is used for the average acceleration value of the first axis. A fourth byte is used for the average acceleration value of the second axis. A fifth byte is used for the maximum acceleration point of the first axis. A sixth byte is used for the maximum acceleration point of the second axis.

Decision block 335 inquires as to whether or not it is time to take a heart rate sample. In one embodiment, the time between heart rate samples is 15 seconds, or once every 8 acceleration samples, but the time can be shorter, longer, or adaptive depending on the activity monitored. When it is not time to take a heart rate sample, program execution branches to step 320 above. If it is time to take a heart rate sample, the number of heart beats since the last time is read and saved in processor internal RAM, as provided in step 340. At this time an additional byte of information containing status information is saved in RAM. The information can be a simple count or it can contain information on an adaptive sampling and/or data rate.

Decision block 345 determines whether or not it is time to save the data that is in processor internal RAM into external storage RAM. If it is not time to store data to external storage RAM, program execution branches to step 320 above. If it is time to store data to external storage RAM, program execution continues to step 350 where data stored in internal processor RAM is transferred to external storage RAM, the external RAM being either volatile or nonvolatile RAM. In one embodiment, the time between storing data to eternal storage RAM is 1 minute, or once every four heart rate samples, but the time can be shorter, longer, or adaptive depending on the activity being monitored.

At decision block 355, the receiver buffer is checked for a valid download command. If a valid download character is not in the buffer, program execution branches to step 320 above. If a valid download character is present in the buffer, program execution continues to step 360 where data from the external storage and internal processor RAM is downloaded to the home base. As explained above, the data may be downloaded through a variety of ways, including using physical wires, an IR link, an RF link or any other means whereby data can be transmitted. In step 720, the external data storage and internal processor RAM are reset and the program branches to step 305 above.

Figure 4:
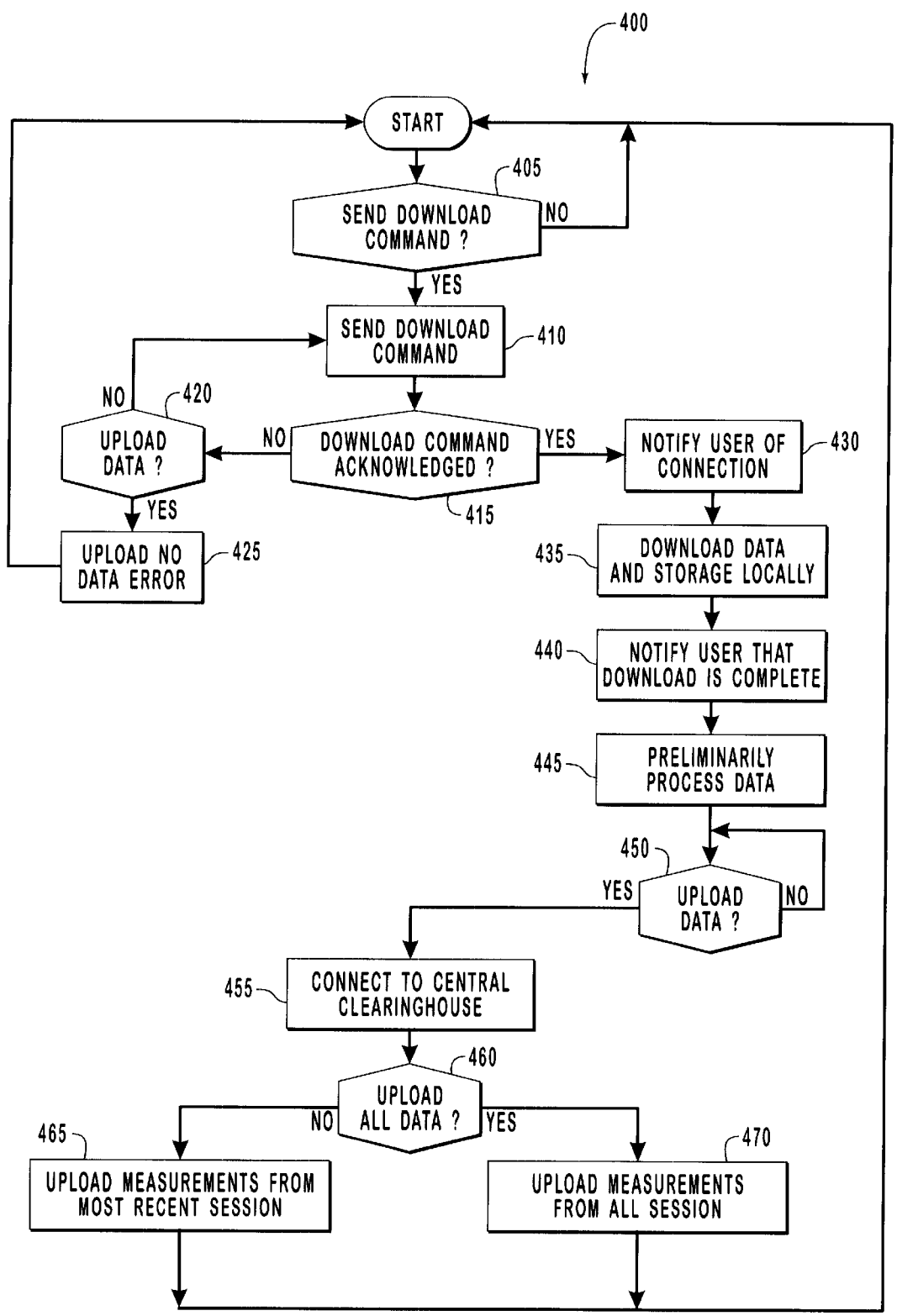
FIG. 4 is a flow chart illustrating a method for uploading measured data from a local storage device to a central clearinghouse, according to one embodiment of the present invention.
Figure 5A:
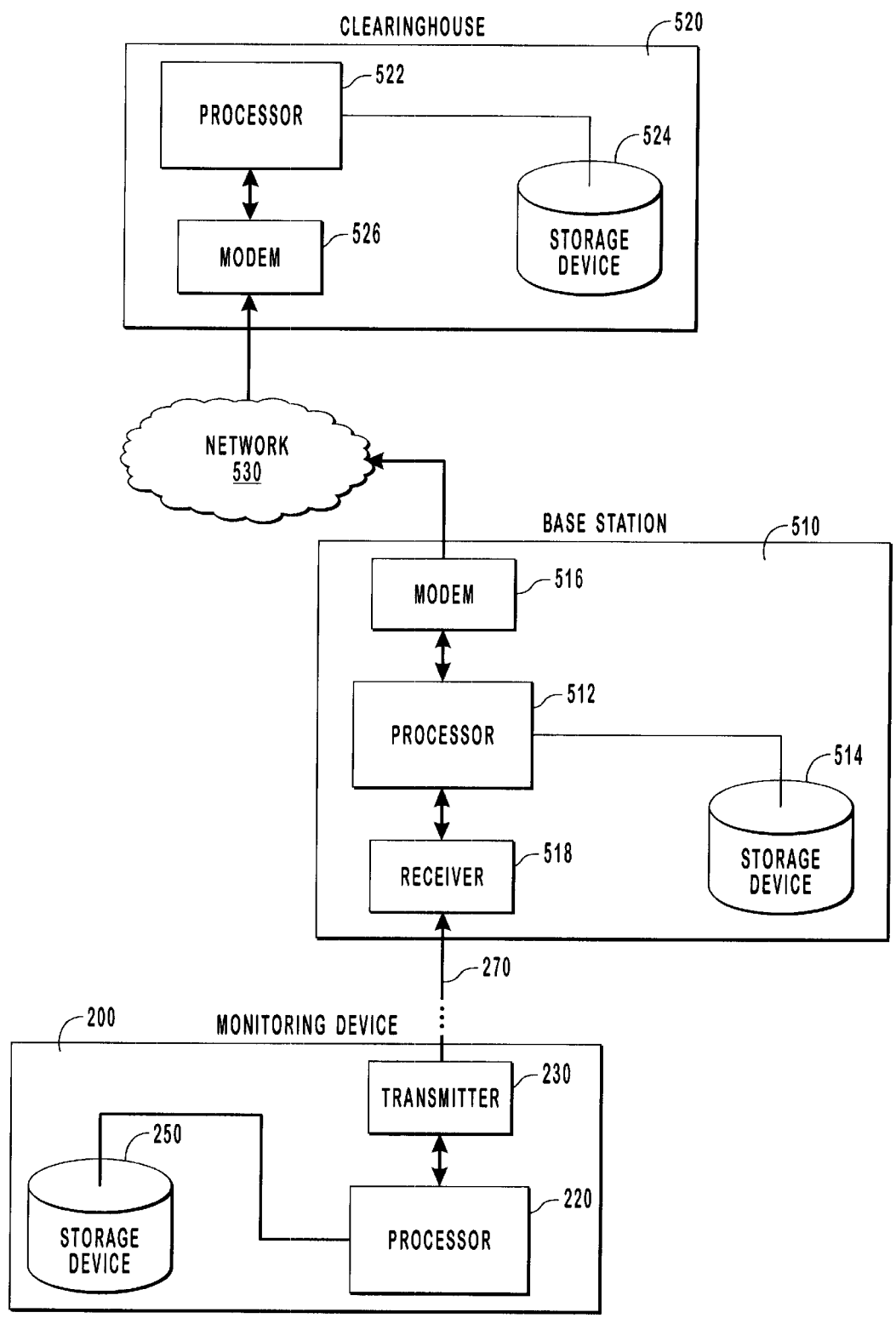
FIG. 5A is a schematic drawing of a monitoring device coupled to a base station that is connected to a central clearinghouse via a network.

Referring now to FIG. 4, a flow chart is provided to illustrate an embodiment where the measured heart rate and acceleration outputs are transmitted or uploaded to and processed at a central clearinghouse. FIG. 5A provides a schematic drawing of a monitoring device coupled to a base station that is connected to a central clearinghouse via a network, and will be used concurrently with FIG. 4 for providing a disclosure of downloading and uploading the output information.

In the embodiment of FIG. 4, the outputs are stored on storage device 250 within monitoring device 200 that is coupled to base station 510 through link 270. Decision block 405 determines whether or not it is time to send a download command from base station 510 to monitoring device 200. If it is not time to send the download command, base station 510 waits until it is time to send a download command. In one embodiment, the time to send the download command is continuous, however the time could be adaptive depending on the activity monitored. Once it is time to send a download command, program execution continues to step 410 for sending the download command to monitoring device 200. The command can be sent in a variety of ways, for example, through the use of physical wires, an IR link, an RF link or any other means for sending a signal.

Decision block 415 then checks for a valid acknowledgement of the download command from monitoring device 200. If a valid acknowledgement is received, program execution branches to step 430 below. If a valid acknowledgement is not received, decision block 420 checks to see if it is time to upload data to clearinghouse 520 via network 530. By way of example, network 530 can be telephone lines, a local area network, a satellite system, the Internet, or any means whereby information can be transmitted from base station 510 to clearinghouse 520. In an embodiment where network 530 is a telephone line connection, base station 510 and clearinghouse 520 respectively utilize modems 516 and 526 to communicate. Furthermore, a visual or audible notification can be sent to the user to notify the user that the telephone lines are being used for an upload and can notify the user of the completion of the upload. If decision block 420 determines that it is not time to upload the data to clearinghouse 520, program execution branches back to step 410 above. If decision block 420 determines that it is time to upload data to clearinghouse 520, program execution continues to step 425 which provides an error because there is no data to upload since it has not yet been downloaded from monitoring device 200 to base station 510, and program execution branches back to decision block 405 above. In one embodiment, information is uploaded once per day from base station 510 to clearinghouse 520, however the frequency with which the uploading takes place can be shorter, longer, or adaptive depending on the activity monitored.

If decision block 415 determines that a valid acknowledgement of the download command from monitoring device 200 has been received, step 430 provides a notification to the user that monitoring device 200 and base station 510 are connected. By way of example, the notification can be audible or visual. With monitoring device 200 connected to base station 510, processor 220 employs transmitter 230 to download the heart rate and acceleration outputs stored on mass storage 250 to base station 510, as provided by step 435. The download can take place, by way of example, through the utilization of physical wires, an IR link, an RF link or any other means for transmitting information. The heart rate and acceleration output information is received by receiver 518 via communication link 270. Processor 512 then stores the heart rate and acceleration output information on storage device 514 and notifies the user that the transmission is complete in step 440. As above, the notification, by way of example, can be visual or audible. In one embodiment of the present invention base station 510 is a single board computer that allows for preliminary processing, as illustrated by step 445. As such, the processing can include compressing data to reduce the time for uploading the information, providing preliminary data reduction, encrypting the data, providing a unique identification of the base station used for the upload, stamping the information with identity information of the individual measured, or organizing the information into a standard data format.

Decision block 450 inquires at to whether or not it is time to upload the heart rate and acceleration outputs to clearinghouse 520. As mentioned above, in one embodiment, the heart rate and acceleration outputs are uploaded once each day. If it is not time for the upload, decision block 450 waits until it is time to upload the outputs. Once it is time to upload the heart rate and acceleration outputs to clearinghouse 520, base station 510 connects to clearinghouse 520 via network 530 in step 455.

Once base station 510 is connected to clearinghouse 520, decision block 460 inquires as to whether or not all of the heart rate and acceleration output information should be downloaded to clearinghouse 520. In one embodiment, storage device 514 maintains all of the heart rate and acceleration information that has been downloaded and can be used as a backup in the event that information is lost at clearinghouse 520. If all of the data stored on storage device 514 is to be uploaded to clearinghouse 520, processor 512 uploads all of the information stored on storage device 514 via network 530 to clearinghouse 520 in step 470. If only the most current information is to be uploaded to clearinghouse 520, step 465 provides for processor 512 to upload the most recent information received from monitoring device 200.

Figure 5B:
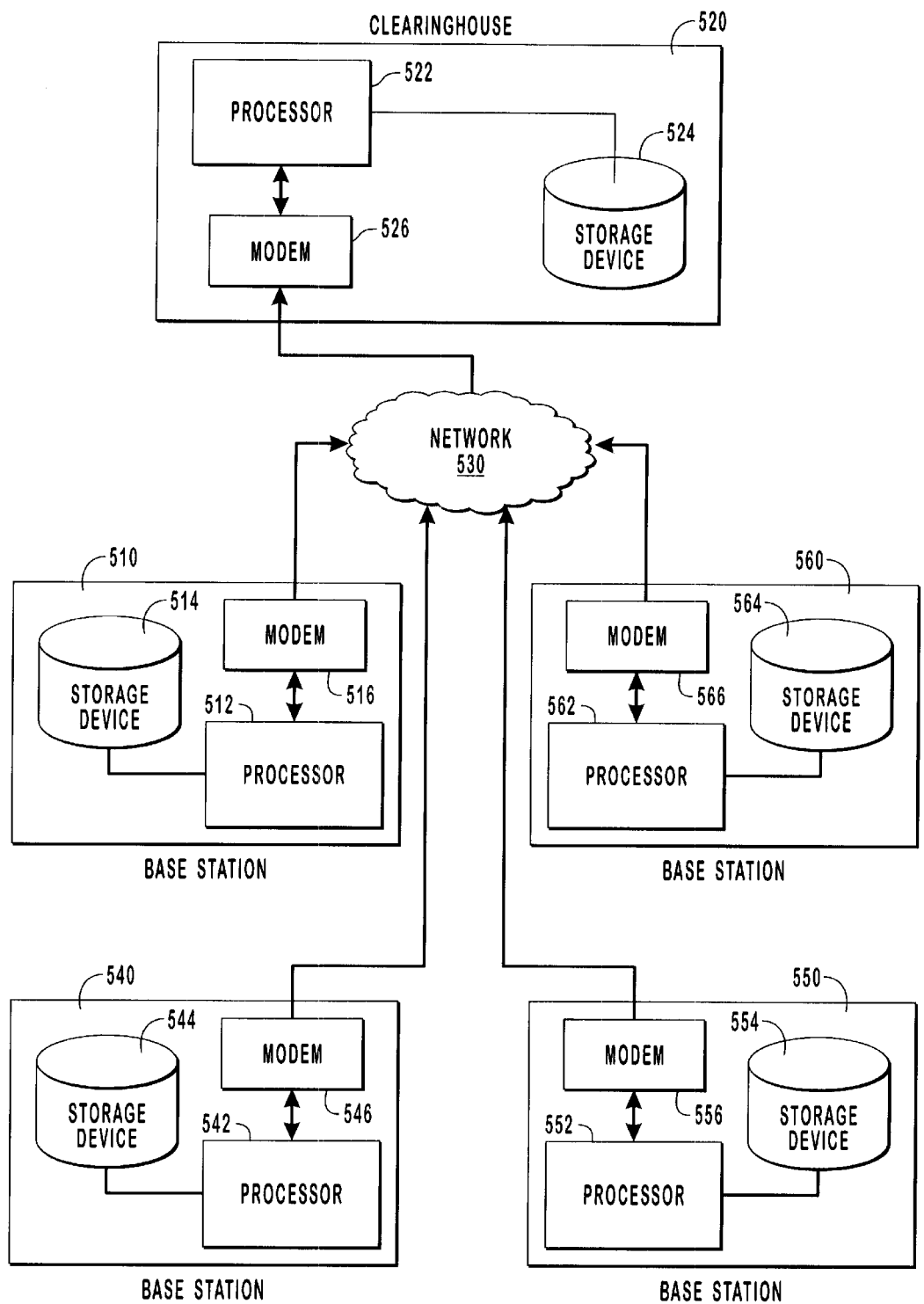
FIG. 5B is a schematic drawing of various base stations connected via a network to a central clearinghouse.

Referring now to FIG. 5B, an embodiment of the present invention is illustrated that provides various base stations connected via a network to a central clearinghouse. Base stations 510, 540, 550, and 560 independently receive heart rate and acceleration information from independent monitoring devices, and each base station uploads information to clearinghouse 520 in a similar manner as was explained above in correlation to FIGS. 4 and 5A. Processor 522 receives all of the information and stores it on storage device 524.

Once the heart rate and acceleration output information is uploaded to clearinghouse 520 and stored on storage device 524, the output information is ready to be processed and used to determine the rate of oxygen consumption as a measurement for the work performed by the individual's body. For ease in providing the disclosure, the information obtained from the accelerometer has been referred to as "acceleration information," "acceleration output" or "acceleration output information." More specifically, the accelerometer output is acceleration information that can be mathematically manipulated to provide activity information used in determining an individual's rate of oxygen consumption in order to measure the amount of work that is performed by the individual's body.

Figure 6A:
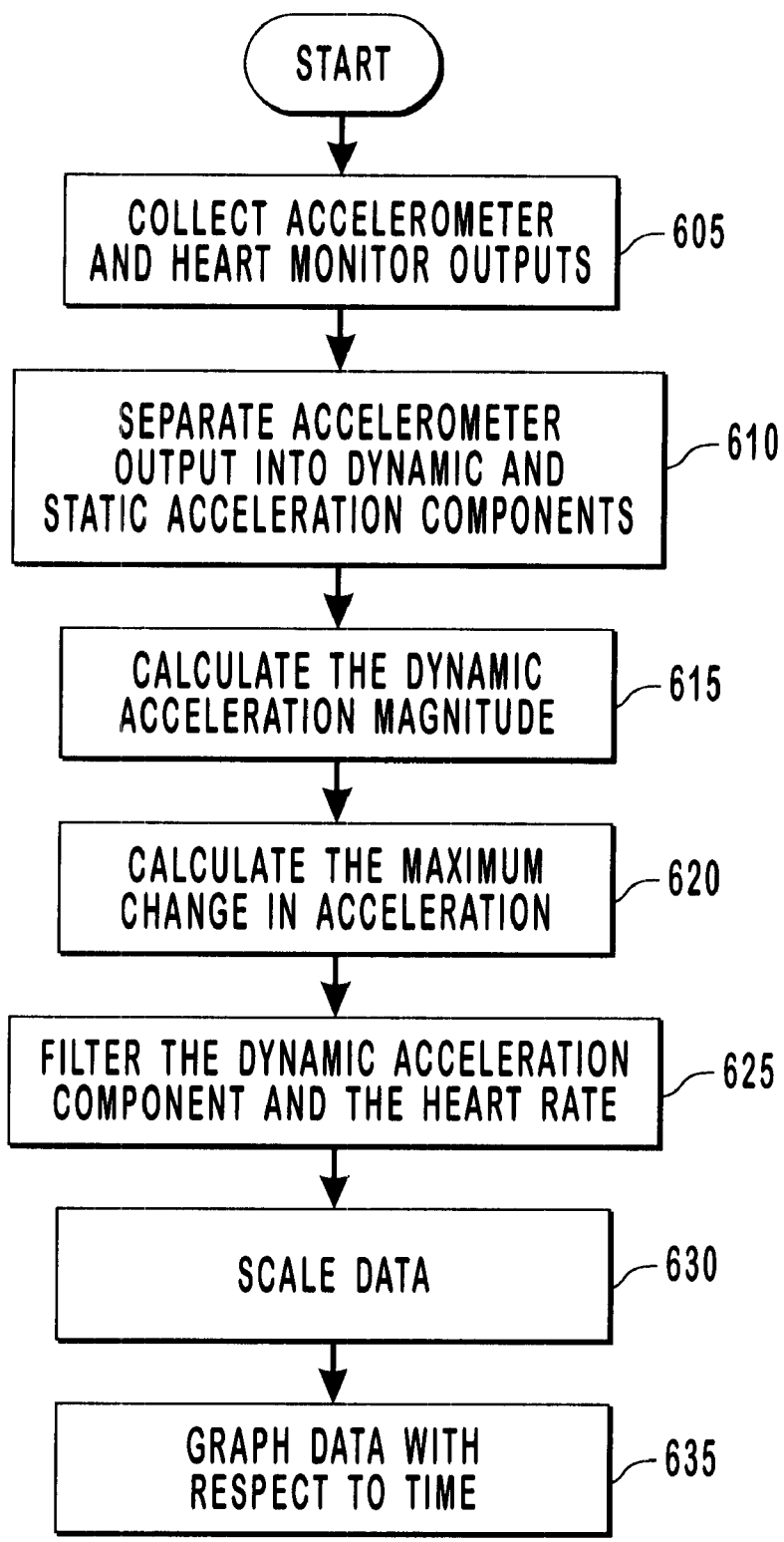
FIG. 6A is a flow chart illustrating a first method for processing the information measured.
Figure 6B:
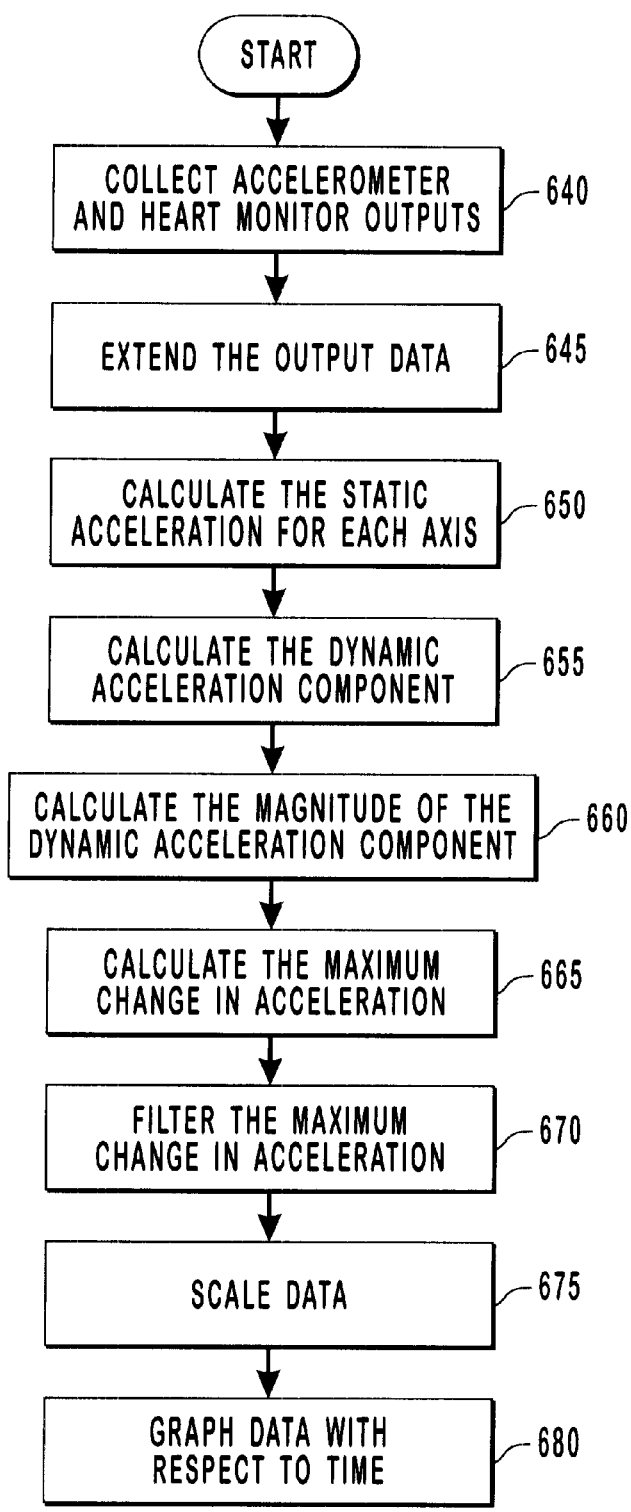
FIG. 6B is a flow chart illustrating a second method for processing the information measured.

FIGS. 6A and 6B provide embodiments illustrating the processing of the output information. The embodiments are for illustrative purposes and should not be construed as limiting the scope of the present invention. In the embodiments illustrated in FIGS. 6A and 6B, mathematical manipulation is done in a mathematically intensive computer program, such as MathCAD.

Referring first to FIG. 6A, outputs are measured from an accelerometer located at an individual's back, an accelerometer located at the individual's side, and from a heart monitor. In step 605 the outputs from the accelerometers and the heart monitor are received by clearinghouse 520, stored on storage device 524, and placed into arrays. The arrays include three columns, namely ouput from the accelerometer located at the individual's back, the output from the accelerometer located at the individual's side, and the output from the heart monitor. More specifically, the outputs are placed into arrays through the use of the following equations:

For the output from the accelerometer located at the individual's back:

Input B:=READPRN ("greg-be.dat")

N:=last (Input $B^{<0>}$)

N=20377

READPRN is a function command in MathCAD to read in the acceleration output data named greg-be.dat. N is the number of rows in the array. The value of N corresponds to the amount of data measured. In this embodiment the value of N is 20377.

For the output measured from the accelerometer located at the individual's side:

Input S:=READPRN ("greg-se.dat")

M:=last (Input S$^{<0>}$)

M=20528

READPRN reads in the acceleration output data named greg-se.dat. M is the number of rows in the array. The value of M corresponds to the amount of data measured. In this embodiment the value of M is 20528.

For the output obtained from the heart monitor:

Manual:=READPRN ("greg.txt")

O:=last (Manual$^{<0>}$)

O:=446

READPRN reads in the heart monitor output data named greg.txt. O is the number of rows in the array. The value of O corresponds to the amount of data measured. In this embodiment the value of O is 446.

Therefore, three data sets are created: Acceleration data from the accelerometer at the individual's back (location "B"); Acceleration data from the accelerometer at the individual's side (location "S"); And heart rate data from the heart monitor. The two accelerometers independently measure data and can provide differing amounts of acceleration data, as noted above by the fact that N and M do not have the same values. Each set of acceleration data consists of two orthogonal axes of acceleration data. In the equations below, the two types of orthogonal axes will be labeled such that one is an x-axis and the other is a y-axis.

Also included in the mathematical calculations of this embodiment, as will be utilized in equations below, are three counters, namely:

i:=0, 1 . . . N j:=0, 1 . . . M o:=0, 1 . . . O

In step 610, the outputs from the accelerometers are separated into their static and dynamic components. The static component can be used to determine the position of the monitor with respect to the ground while the dynamic acceleration data can be used to determine the activity, or energy expenditure, of the individual. The mean or average acceleration for each axis is calculated, representing the static acceleration for the respective axis. In this embodiment the mean acceleration is calculated for the entire data set. Alternatively, in another embodiment, the mean can be calculated over a subset of the data and would thereby represent the change in position during the monitoring period. The subset can be sequential or can be a moving subset for the monitoring period.

The dynamic acceleration is calculated by subtracting the calculated static acceleration from the total measured acceleration. If the static acceleration is calculated over a subset of the data, the static data is subtracted from the corresponding total measured acceleration in order to obtain the dynamic component. The following equations can be employed in MathCAD to separate the components:

For the output measured from the accelerometer located at the individual's back:

Mean_B$_x$:=mean(Input_B$^{<0>}$)

Mean_B$_x$=0.531

Mean_B$_y$:=mean(Input_B$^{<1>}$)

Mean_B$_y$=0.414

Input_B_cal$_{j,0}$:=(Input_B$_{j,0}$)−Mean_B$_x$

Input_B_cal$_{j,1}$:=(Input_B$_{j,1}$)−Mean_B$_y$

Input_B$^{<0>}$ represents the data points measured in the x-direction and Input_B$^{<1>}$ represents the data points measured in the y-direction. Mean_B$_x$ is the mean value measured for the x-axis and represents the static acceleration in that direction. Mean_B$_y$ is the mean value measured for the y-axis and represents the static dynamic acceleration in that direction. Input_B_cal$_{j,0}$ represents the dynamic acceleration in the x-direction and Input_B_cal$_{i,1}$ represents the dynamic acceleration in the y-direction.

For the output measured from the accelerometer located at the individual's side:

Mean_S$_x$:=mean(Input_S$^{<0>}$)

Mean_S$_x$=0.56

Mean_S$_y$:=mean(Input_S$^{<1>}$)

Mean_S$_y$=0.507

Input_S cal$_{j,0}$:=(Input_S$_{j,0}$)−Mean_S$_x$

Input_S cal$_{j,1}$:=(Input_S$_{j,1}$)−Mean_S$_y$

Input_S$^{<0>}$ represents the data points measured in the x-direction and Input_S$^{<1>}$ represents the data points measured in the y-direction. Mean_S$_x$ is the mean value measured for the x-axis thereby providing the static acceleration in that direction. Mean_S$_y$ is the mean value measured for the y-axis thereby providing the static acceleration in that direction. Input_S_cal$_{i,0}$ represents the dynamic acceleration in the x-direction and Input_S cal$_{i,1}$ represents the dynamic acceleration in the y-direction.

In step 615, the dynamic acceleration magnitude is calculated by using the dynamic acceleration components for both the x-axis and the y-axis of each accelerometer as calculated in step 610. The magnitude can be calculated through the use of the following equations:

For the output measured from the accelerometer located at the individual's back:

$$\text{Input\_B\_2}d_i := \sqrt{(\text{Input\_B\_cal}_{i,0})^2 + (\text{Input\_B\_cal}_{i,1})^2}$$

For the output measured from the accelerometer located at the individual's side:

$$\text{Input\_S\_2}d_j := \sqrt{(\text{Input\_S\_cal}_{j,0})^2 + (\text{Input\_S\_cal}_{j,1})^2}$$

In step 620, the maximum change in acceleration within a time interval is calculated. In this embodiment, the maximum change is calculated for sequential sets of 20 data points corresponding to a time interval of 1 second, however the number of data points could be changed depending on the sample rate of the input data. The maximum change is mathematically calculated through the use of the following equations and parameters:

For the output from the accelerometer located at the individual's back:

Input_B_MM$_k$ is the maximum change in acceleration, n is the maximum number of data points, and k is a counter.

$$n := \text{floor}\left(\frac{\text{last}(\text{Input\_B\_2d}_i)}{20}\right) - 1$$

n=1.017×10$^3$ k:=0,1 ... n

Input_B_MM$_k$:=max(submatrix(Input_B_2d$_P$, k·Size, ((k+1)·Size)−1,0,0))

−min(submatrix(Input_B_2d$_P$, k·Size, ((k+1)·Size)−1,0,0))

For the output from the accelerometer located at the individual's side:

$$m := \text{floor}\left(\frac{\text{last}(\text{Input\_S\_2d}_i)}{20}\right) - 1$$

m=1.093×10$^3$ l:=0,1 ... m

Input_B_MM,:=max(submatrix(Input_S__2d$_F$, l·Size, ((l+1)·Size)−1,0,0))

−min(submatrix(Input_S_2d$_F$, l·Size, ((l+1)·Size)−1,0,0))

Input_B_MM$_l$ is the maximum change in acceleration, m is the maximum number of data points, and l is a counter.

In step 625, the heart rate and the maximum change in the dynamic acceleration data, calculated in step 620, are filtered. As demonstrated in this embodiment, an averaging algorithm available in MathCAD, called medsmooth, can be employed for the filtering. Medsmooth is a median smoothing algorithm for vectors or data arrays. The algorithm Medsmooth is a median smoothing algorithm for vectors or data arrays. The algorithm functions within a specified window around a data point. It takes the middle point within the window and calculates the median for the window surrounding that data point. The user is able to specify the size of the window, however it is required that the window size be an odd numbered integer so that a median can be obtained. After the algorithm has obtained a median value for the first point, it goes to the next point in the array and finds the median value for that data point. The process continues for all of the data points. As such, medsmooth provides a moving average over an easily defined window. In one embodiment, a window parameter that has a value of 91 provides a relatively smooth curve for the acceleration data. Therefore, the filtering can be done by the following equations:

window:=91

Accel_Back_F:=medsmooth(Input_B_MM$_k$, window)

Accel_Side_F:=medsmooth(Input_S_MM$_l$, window)

The parameter window is the window value for the measured output. Accel_Back_F is the filtered maximum change in acceleration obtained from the accelerometer located at the individual's back. Accel_Side_F is the filtered maximum change in acceleration obtained from the accelerometer located at the individual's side.

A comparison can be made between an embodiment of the present invention and traditionally measured VO2 data. Because the rate for which measurements are taken using the traditional method differs from the rate used by embodiments of the present invention, a new window parameter is established in order to utilize medsmooth to scale the traditionally measured data in order for the comparison to be made. In one embodiment, a window parameter that has a value of 41 provides a relatively smooth curve for the traditionally measured data. Thus, the traditionally measured data is filtered by using the following equations:

psy_win:=41

HR filt:=medsmooth(Manual$^{<6>}$, psy_win)

VO2 filt:=medsmooth(Manual$^{<11>}$, psy_win)

The parameter psy_win is the window value for the traditionally measured data. HR_filt represents the filtered heart rate and VO2_filt represents the filtered VO2 data.

In step 630, the data is converted to the same units. In one embodiment, the acceleration data can be scaled to VO2 data by entering a scale and offset factor based upon the physiological parameters of the individual. In another embodiment, all of the data is normalized from 0 to 1. This is done mathematically through the use of the following equations:

For the information that was obtained and determined by an embodiment of the present invention:

$$AB\_Filter_k := \frac{(Accel\_Back\_F_k - Accel\_Back\_F_0)}{\max(Accel\_Back\_F) - Accel\_Back\_F_0}$$

$$AS\_Filter_l := \frac{(Accel\_Side\_F_l - Accel\_Side\_F_0)}{\max(Accel\_Side\_F) - Accel\_Side\_F_0}$$

AB_Filter$_k$ is the filtered and scaled acceleration data obtained from the accelerometer located at the individual's back and AS_Filter$_l$ is the filtered and scaled acceleration data obtained from the accelerometer located at the individual's side.

For the information that was traditionally measured:

$$HR\_Filter_o := \frac{(HR\ filt_o - HR\ filt_o)}{\max(HR\ filt) - HR\ filt_o}$$

$$VO2\_Filter_o := \frac{(VO2\ filt_o - VO2\ filt_o)}{\max(VO2\ filt) - VO2\ filt_o}$$

$$HR_o := \frac{(Manual_{o,6} - HR\ filt_o)}{\max(HR\ filt) - HR\ filt_o}$$

$$VO2_o := \frac{(Manual_{o,11} - VO2\ filt_o)}{\max(VO2\ filt) - VO2\ filt_o}$$

HR$_o$ represents the scaled heart rate data and VO2$_o$ represents the scaled VO2 data, HR_Filter$_o$ represents the filtered and scaled heart rate data, and VO2_Filter$_o$ represents the filtered and scaled VO2 data.

In step 635, the data is graphed with respect to time to generate a graphical representation of the VO2, the rate of oxygen consumption of the individual, and to provide a comparison between an embodiment of the present invention and the traditional method. When graphing, all plots should have the same base unit for time in order that the comparison between VO2, or activity, and heart rate can be accurately made. A graphical comparison will be provided as part of the embodiment referred to in FIG. 6B.

Referring now to FIG. 6B, a flow chart illustrates the processing of an embodiment where only acceleration information is measured and processed, and where the output of the accelerometer includes data from two orthogonal axes. In the example below, one axis will referred to as the x-axis and the other as the y-axis. In step 640, the accelerometer output is received by clearinghouse 520, stored on storage device 524 and placed into an array. (Clearinghouse 520 and storage device 524 are illustrated in FIGS. 5A and 5B.) The array includes two columns, namely an x-axis duty cycle that goes from 0 to 1 and a y-axis duty cycle the goes from 0 to 1. The accelerator output is placed into an array through the use of the following equations:

Input_B:=READPRN("greg-b.dat")

N:=last(Input_B$^{<0>}$)

N:=16677

READPRN is a functional command in MathCAD for reading in the output file entitled greg-b.dat and N is the number of rows in the array. The value of N corresponds to the amount of data measured. In this embodiment the value of N is 16677.

In step 645, the data output is extended before the start and after the end of the recorded data in order to obtain a smooth plot. In one embodiment, a macro is created that repeats the first 20 data points about 1800 times before the beginning and after the end of the existing data array thereby creating a new data array. The parameters employed are:

size:=20 n:=0, 1 . . . N d:=0, 1 . . . 1799

Size represents the number of data points that are repeated, n is a counter, and d is the number of times that the data points are repeated. Having set the parameters, the data can be extended by using a mathematical program, such as MathCAD. The equations to extend the data include:

Fill_S:=submatrix(Input_B, 0, size−1, 0, 1 )

Fill_E:=submatrix(Input_B, N,−size+1, N, 0, 1)

Start_Fill$_{d,0}$:=Fill_S$_{mod(size)0}$

End_Fill$_{d,0}$:=Fill_E$_{mod(size)0}$

Start_Fill$_{d,1}$:=Fill_S$_{mod(size)1}$

End_Fill$_{d,1}$:=Fill_E$_{mod(size)1}$

A$^{<0>}$:=stack(Start_Fill$^{<0>}$,Input_B$^{<0>}$)

A$^{<1>}$:=stack(Start_Fill$^{<1>}$,Input_B$^{<1>}$)

Extn_B$^{<0>}$:=stack(A$^{<0>}$,End_Fill$^{<0>}$)

Extn_B$^{<1>}$:=stack(A$^{<1>}$,End_Fill$^{<1>}$)

M:=lastExtn_B$^{<0>}$

M=20277 m:=0, 1 . . . M

WRITEPRN("greg-bme.dat"):=Extn_B

Fill_S allows for the extension at the beginning of the axes and Fill_E allows for the extension at the end of the axes. Start_Fill$_{d,0}$ represents the data extended at the beginning of the x-axis and Start_Fill$_{d,1}$ represents the data extended at the beginning of the y-axis. End-Fill$_{d,0}$ represents the data extended at the end of the x-axis and End__Fill$_{d,1}$ represents the data extended at the end of the y-axis. A$^{<0>}$ links Star_Fill$_{d,0}$ with the original x-axis data and A$^{<1>}$ links Start_Fill$_{d,1}$ with the original y-axis data. Extn_B$^{<0>}$ links A$^{<0>}$ with End-Fill$_{d,0}$ in order to provide the total number of data points for the x-axis. Extn_B$^{<1>}$ links A$^{<1>}$ with End__Fill$_{d,1}$ in order to provide the total number of data points for the y-axis. M is the total number of data points for each axis and m is a counter.

Figure 7:
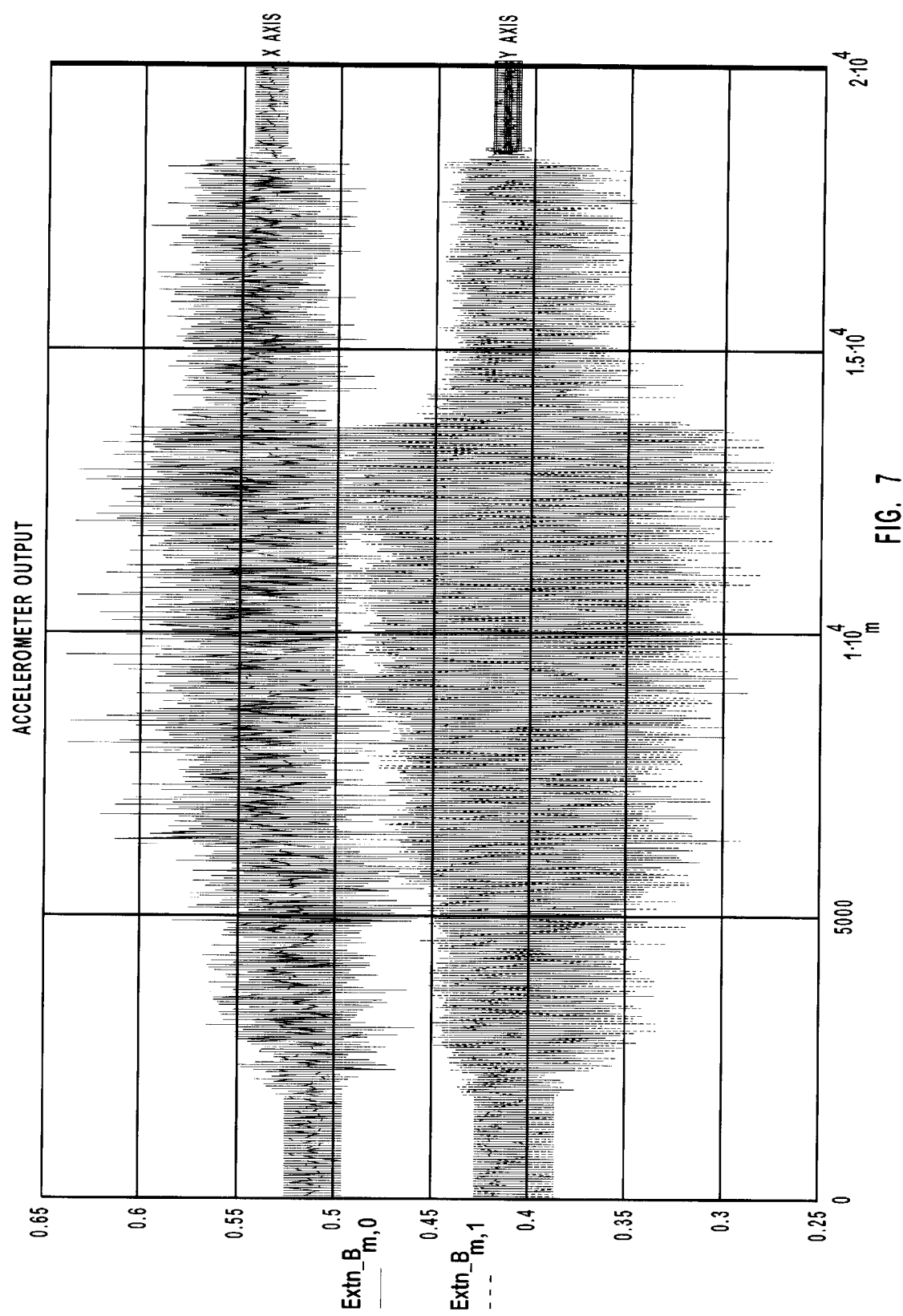
FIG. 7 is a plot illustrating the output data from an accelerometer for a first and second axis, the data points having been extended at the beginning and ending of the outputs.

FIG. 7 provides a plot that illustrates the addition of the extended data points for both the x-axis and the y-axis. The new data array is 20277 data points long. On the plot, Extn__B$_{m,0}$ represents the output for the x-axis and Extn__B$_{m,1}$ represents the output for the y-axis. Furthermore, the graph represents units verses time.

Referring back to FIG. 6B, step 650 provides for the calculation of the static acceleration of each axis. The process more specifically provides an AC coupling to the input data. The mean acceleration for each axis is calculated for determining the static acceleration for the respective axis, and can be used to determine the position of the accelerometer with respect to the ground. As mentioned above, the mean can be calculated over a subset of the data to represent the change in position during the monitoring period.

The mean value is calculated for a running window from the start of the array through the end of the array. By way of example, this can be done by utilizing a moving mean algorithm, a median of consecutive data sections, or an average of consecutive data sections. In the embodiment where MathCAD is used to perform the calculations it should be noted that medsmooth does not work at the extreme ends of the input data file. As such, the arithmetic mean is used for those extreme data points. This is done mathematically through the use of the following equations and parameters:

Avg_win:=11

$$Break_1 := \frac{(Avg\_win-1)}{2}$$

$$Break_2 := N \frac{(Avg\_win+1)}{2}$$

n$_s$:=0,1 . . . Break$_1$ n$_m$:=Break$_1$+1, Break$_1$+2 . . . Break$_2$ n$_e$:=Break$_2$+1, Break$_2$+2 . . . N Avg$_{sx}$:=mean(submatrix(Extn_B, 0, Break$_1$, 0, 0))

Avg$_{sx}$:=0.513

Avg$_{sy}$:=mean(submatrix(Extn_B, 0, Break$_1$, 1, 1))

Avg$_{sy}$:=0.417

Avg$_{ex}$:=mean(submatrix(Extn_B, Break$_2$,+1, N, 0, 0))

Avg$_{ex}$:=0.537

Avg$_{ey}$:=mean(submatrix(Extn_B, Break$_2$,+1, N, 1, 1))

Avg$_{ey}$:=0.415

Avg$_m{}^{<0>}$:=medsmooth(Extn_B$^{<0>}$, Avg_win)

Avg$_m{}^{<1>}$:=medsmooth(Extn_B$^{<1>}$, Avg_win)

Avg_win is the length of a sub matrix of data to which medsmooth is used is used to calculate the moving median. $Avg_m^{<0>}$ represents the static acceleration for the x-axis and $Avg_m^{<1>}$ represents the static acceleration for the y-axis. $Avg_{sx}$ is the average value of a running window at the start of the data set for the x-axis and has a value of 0.513 in the embodiment. $Avg_{sy}$ is the average value of a running window at the start of the data set for the y-axis and has a value of 0.417 in the embodiment. $Avg_{ex}$ is the average value of a running window at the end of the data set for the x-axis and has a value of 0.537 in the embodiment. $Avg_{ey}$ is the average value of a running window at the end of the data set for the y-axis and has a value of 0.415 in the embodiment.

Figure 8:
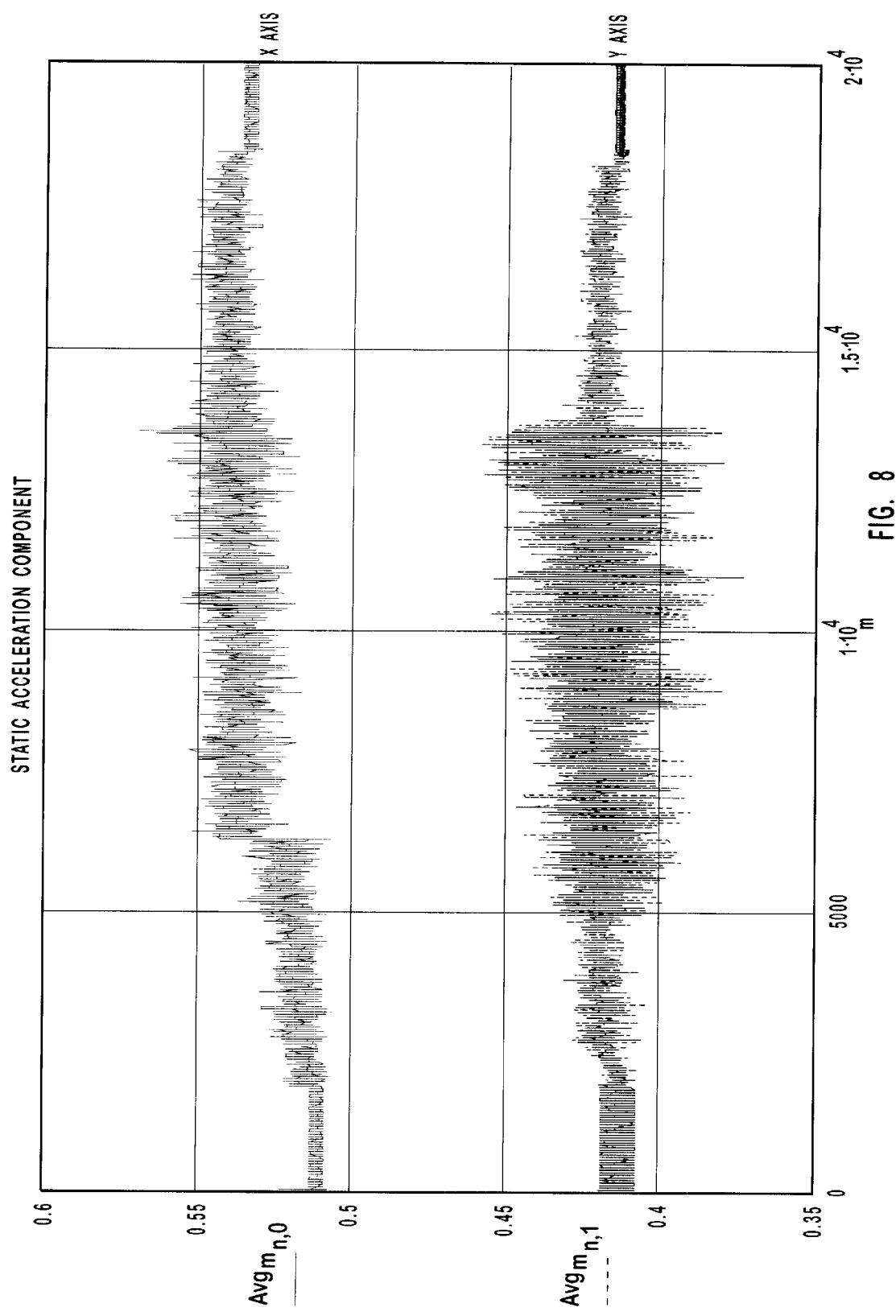
FIG. 8 is a plot illustrating the static acceleration for a first and second axis.

FIG. 8 provides a plot of the static acceleration for the x-axis and for the y-axis. More specifically, the plot provides the moving median for the x-axis and the moving median for the y-axis. $Avg_{mn,0}$ represents the static acceleration for the x-axis and $Avg_{mn,1}$ represents the static acceleration for the y-axis. The plot is illustrated as units versus time.

In step 655, the dynamic acceleration is calculated by subtracting the calculated static acceleration, obtained above in step 650, from the total acceleration. More specifically, the running median data set is subtracted element by element from the input data set in order to obtain an AC coupled data. This removes the effects of the static acceleration from the input data set thereby leaving only the dynamic, or kinetic, acceleration. In one embodiment, the calculations can be accomplished in MathCAD through the use of the following equations:

For the dynamic acceleration of the x-axis:

$$Extn\_B\_AC_{n_s}^{,0}:=Extn\_B_{n_s}^{,0}-Avg_{sx}$$

$$Extn\_B\_AC_{n_m}^{,0}:=Extn\_B_{n_m}^{,0}-Avg_{m_{xm}}^{,0}$$

$$Extn\_B\_AC_{n_s}^{,0}:=Extn\_B_{n_s}^{,0}-Avg_{ex}$$

$Extn\_B\_AC_{ns,0}$ is the beginning AC coupled data set for the x-axis from the beginning of the original data set. $Extn\_B\_AC_{nm,0}$ is the middle AC coupled data set for the x-axis from the middle of the original data set. $Extn\_B\_AC_{ne,0}$ is the ending AC coupled data set for the x-axis from the ending of the original data set.

For the dynamic acceleration of the y-axis:

$$Extn\_B\_A_{n_s}^{,0}:=Extn\_B_{n_s}^{,0}-Avg_{sy}$$

$$Extn\_B\_AC_{n_m}^{,1}:=Extn\_B_{n_m}^{,1}-Avg_{m_{nm}}^{,1}$$

$$Extn\_B\_AC_{n_s}^{,1}:=Extn\_B_{n_s}^{,1}-Avg_{sy}$$

$Extn\_B\_AC_{ns,1}$ is the beginning AC coupled data set for the y-axis from the beginning of the original data set. $Extn\_B\_AC_{nm,1}$ is the middle AC coupled data set for the y-axis from the middle of the original data set. $Extn\_B\_AC_{ne,1}$ is the ending AC coupled data set for the y-axis from the ending of the original data set.

Figure 9A:
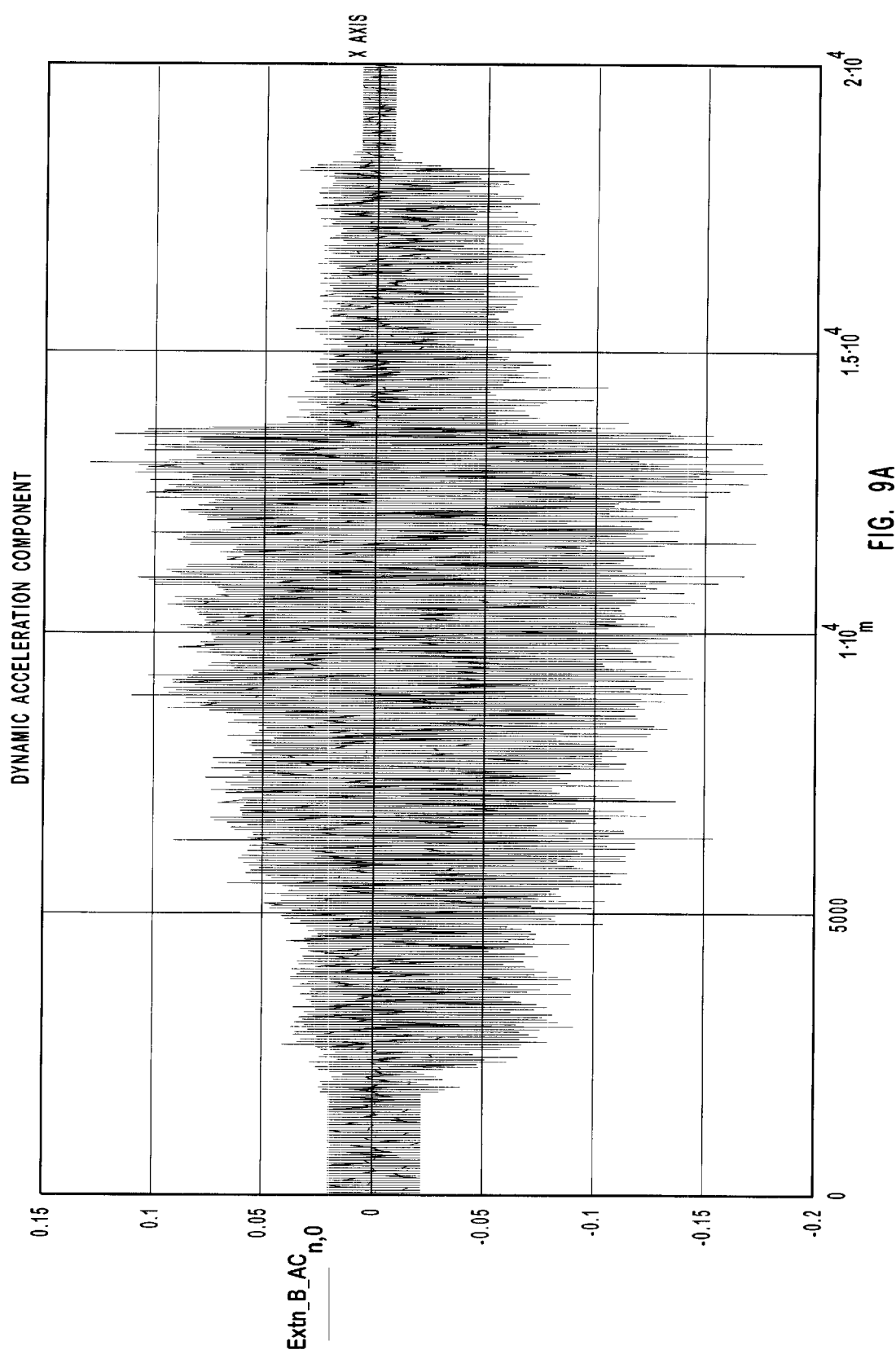
FIG. 9 is a plot illustrating the dynamic acceleration for a first and second axis.
Figure 9B:
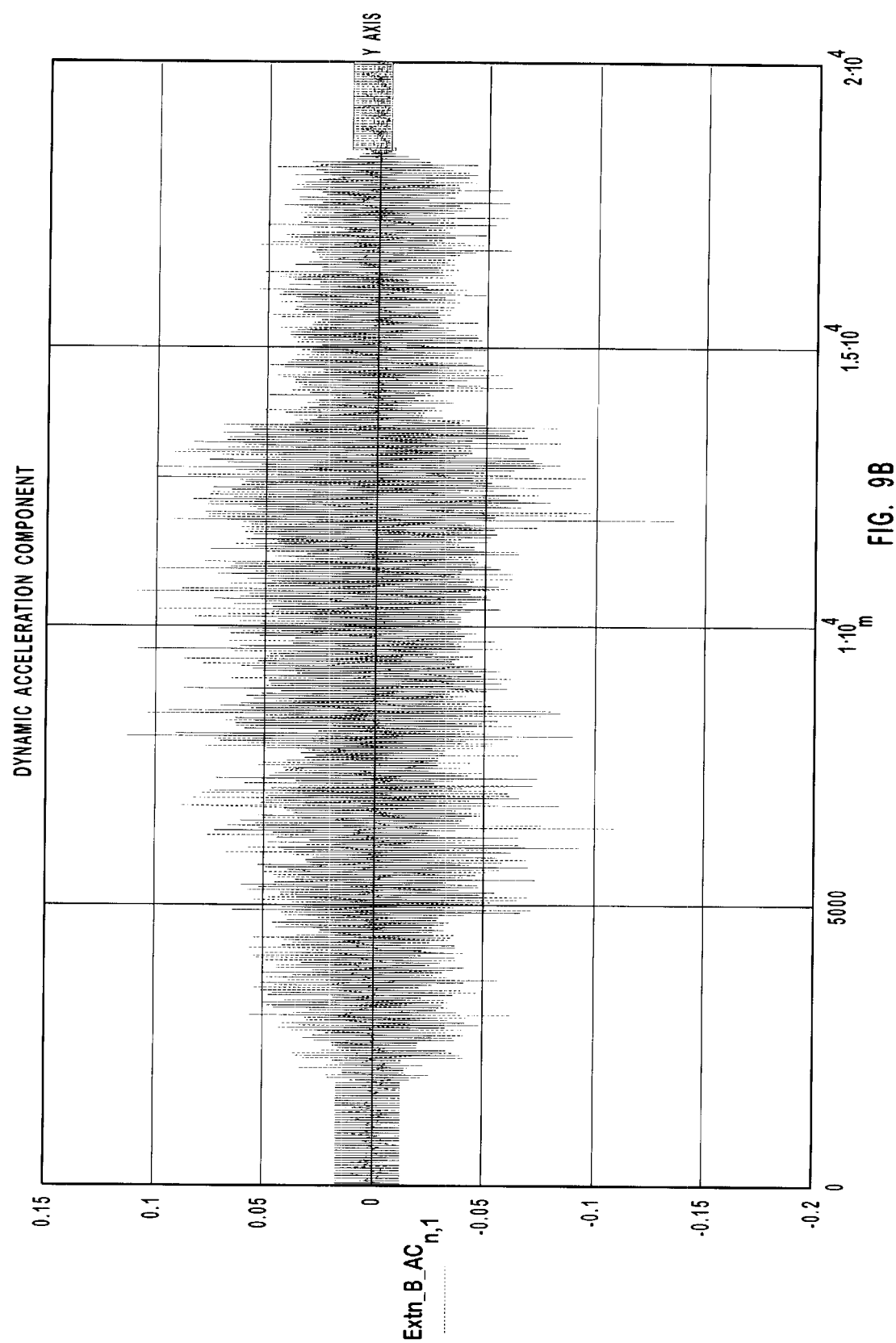

FIG. 9 provides a plot of the dynamic acceleration for the x-axis and for the y-axis. This dynamic acceleration can be used to determine the activity or energy expenditure of the individual. $Extn\_B\_AC_{n,1}$ represents the dynamic acceleration for the x-axis and $Extn\_B\_AC_{n,1}$ represents the dynamic acceleration for the y-axis. The plot is represented as units versus time.

In step 660 the dynamic acceleration magnitude is calculated using the dynamic acceleration data calculated in step 655. In the embodiment where MathCAD is utilized, the dynamic acceleration, known in the present embodiment as Extn_B_AC, can be written into a file and named greg-bme-ac.dat. This file can then be read in and redefined as Input_B, as provided in the following equations:

WRITEPRN ("greg-bme-ac.dat"):=Extn_B_AC

Input_B:=READPRN ("greg-bme-ac.dat")

Since AC coupled data is being utilized, the static acceleration due to gravity and any offsets in the original measurements are subtracted out. In the embodiment, the dynamic acceleration magnitude is calculated through the use of the following equations:

$N:=last\ Input\_B^{<0>}$ $N=20277$ $n:=0,1\ldots N$ $mag_{n,0}:=\sqrt{(Input\_B_{n,0})^2+(Input\_B_{n,1})^2}$ As explained above, N is the number of data points. The value of N is 20277. The variable n is used as a counter. $Input\_B_{n,0}$ is the dynamic acceleration for the x-axis and $Input\_B_{n,1}$ is the dynamic acceleration for the y-axis. The variable magn, represents the dynamic acceleration magnitude for both axes.

In step 665, the maximum change in dynamic acceleration within a time interval is calculated. In one embodiment, the maximum change is calculated for sequential sets of 20 data points corresponding to a time interval of 1 second. In other embodiments the number of data points can be changed depending on the sample rate of the input data. In one embodiment, the maximum change in dynamic acceleration can be calculated in MathCAD through the use of the following equations and parameters:

$Size:=20$ $$m:=floor\left(\frac{last(mag)}{Size}\right)-1$$

$m=1.012\cdot 10^3$ $k:=0,1\ldots m$ $PP_{k,0}:=k$ $PP_{k,1}:\ max(submatrix(mag,\ k\cdot Size,\ ((k+1)\cdot Size)-1,0,0))$ $-min(submatrix(mag,\ k\cdot Size,\ ((k+1)\cdot Size)-1,0,0))$ WRITEPRN("greg-bme-pp.dat"):=PP Size is the number of data samples, m is the maximum number of data points, and k is a counter. $PP_{k,1}$ is the maximum change in dynamic acceleration.

Figure 10:
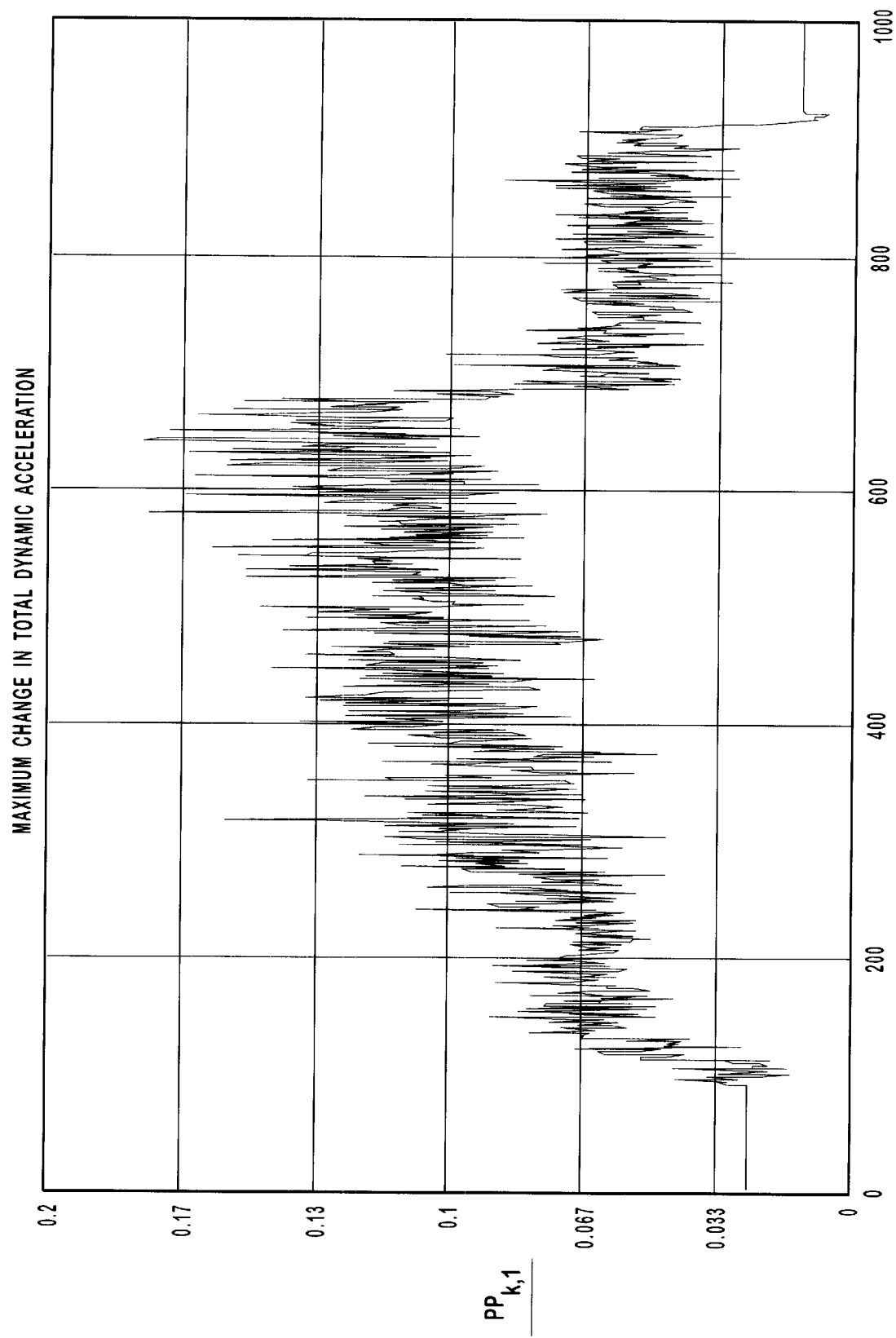
FIG. 10 is a plot illustrating the maximum change in total dynamic acceleration over an interval of time.

The maximum change in dynamic acceleration represents the envelope of the magnitude over an interval of time. FIG. 10 provides a plot of the envelope value for the entire amount of time that measurements were taken. The plot is the general shape of the VO2 profile. In the plot $PP_{k,1}$, represents the maximum change in dynamic acceleration. The plot represents units versus time.

In step 670 the maximum change in the dynamic acceleration data, calculated in step 665, is filtered. The filtering eliminates the noisiness of the VO2 profile. More specifically, in one embodiment a filtering algorithm such as medsmooth, built into MathCAD, is employed. As such, the size of the window around a data point that is used by medsmooth is specified. The size of the window must be an odd integer so that a median integer can be obtained. In one embodiment, the value of 91 provides a relatively smooth curve. The filtering is performed through the following equations and parameters:

$$N := last\ (Input\_PP^{<1>})$$

$$N = 1020$$

$$window := 91$$

$$PP\ filt := medsmooth(Input\_PP^{<1>}, window)$$

N is the last maximum change value for the x-axis, n is a counter, window is the window value for the acceleration data for using the medsmooth function. PP_filt is the filtered maximum change in dynamic acceleration.

Figure 11:
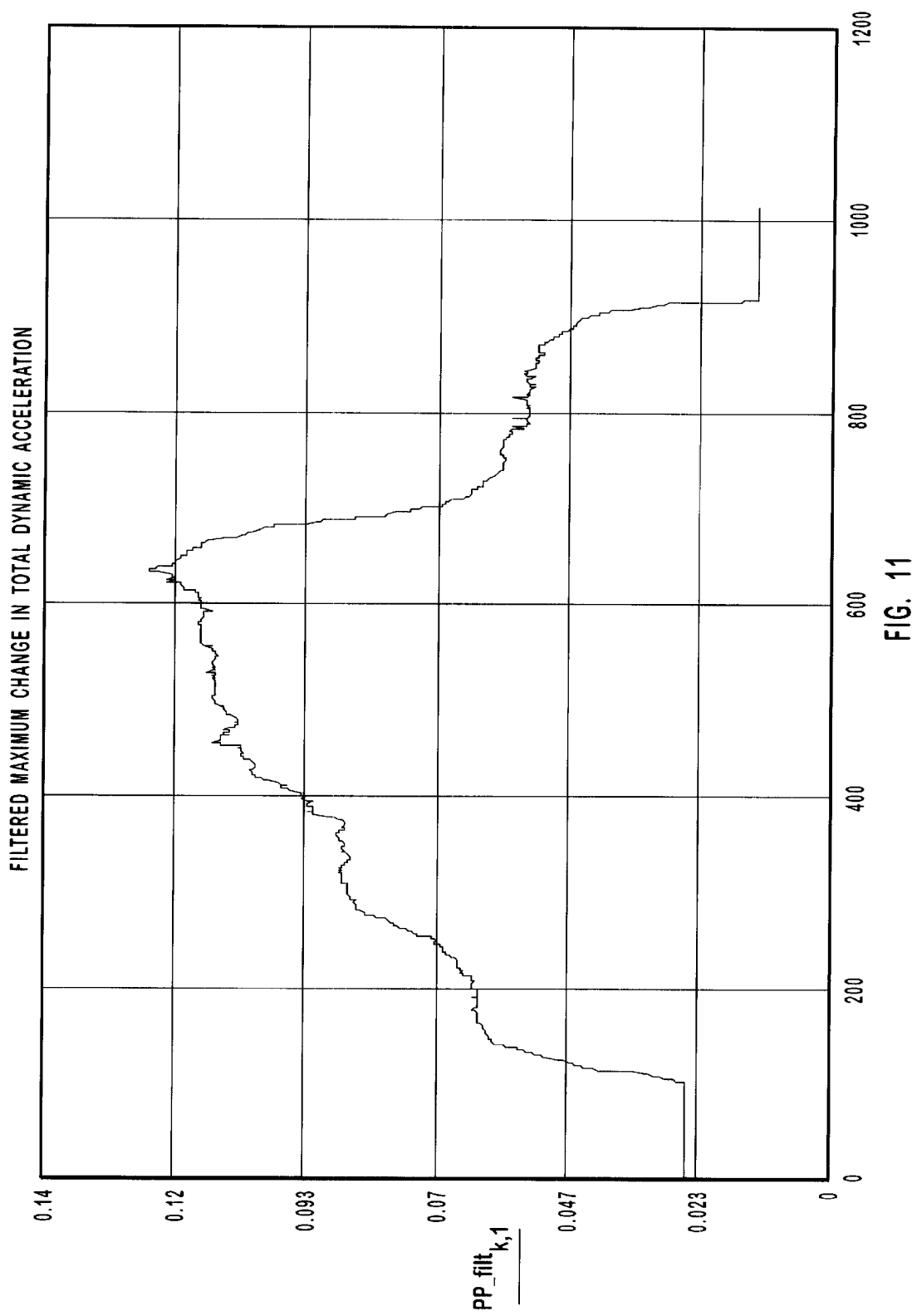
FIG. 11 is a plot illustrating the filtered maximum change in total dynamic acceleration over an interval of time.

FIG. 11 provides a plot of the filtered maximum change in the dynamic acceleration. The plot is the averaged envelope value for the entire period that measurement were taken. In the plot, $PP\_filt_n$ represents the filtered maximum change in dynamic acceleration. The plot is represented as units versus time.

Step 675 allows for a comparison of the results between the traditional method and an embodiment of the present invention. In one embodiment the units from the accelerometer are several orders of magnitude smaller than the units of VO2. Hence, the data from the traditional method is scaled into the same units a the filtered maximum change in dynamic acceleration, obtained above in step 670. In one embodiment the scaling or normalization is performed by defining the initial value of the traditional data set as zero. The maximum value of the traditionally measured data set is defined as one. In one embodiment the medsmooth algorithm of MathCAD is employed However, since the sample rate employed in the traditional method is different to the sample rate used above, a different window size is used. In one embodiment, the window size of 41 for the traditionally measured data achieves the same effective filter bandwidth as the acceleration data above. The acceleration data can also be scaled to VO2 data by entering a scale and offset factor based upon the physiological parameters of the subject. The scale factor and the offset for plotting the normalized, traditionally measured data is defined by the normalization that employs the following equations and parameters:

$$Manual := READPRN\ (\text{"greg.txt"})$$

$$O := last(Manual^{<0>})$$

$$O = 446$$

$$o := 0, 1 \ldots O$$

$$psy\_win := 41$$

$$VO2\_filt := medsmooth(Manual^{<11>}, psy\_win)$$

$$VO2\_Norm_b := \frac{(VO2\ filt_o - VO2\ filt_o)}{\max(VO2\ filt) - VO2\ filt_o}$$

$$PP\_Filt\_Norm_n := \frac{(PP\ filt_n - PP\ filt_n)}{\max(PP\ filt) - PP\ filt_o}$$

The file greg.txt contains the data of the traditionally measured data. O represents the number of traditionally measured data points and o is a counter. The variable psy_win represents the window size used to in medsmooth. VO2_filt represents the traditionally measured data that has been filtered. $VO2\_Norm_o$ represents the traditionally measured data that has been filtered and scaled, or normalized. $PP\_Filt\_Norm_n$ is the filtered maximum change in the dynamic acceleration data of step 670 that has been normalized.

Figure 12A:
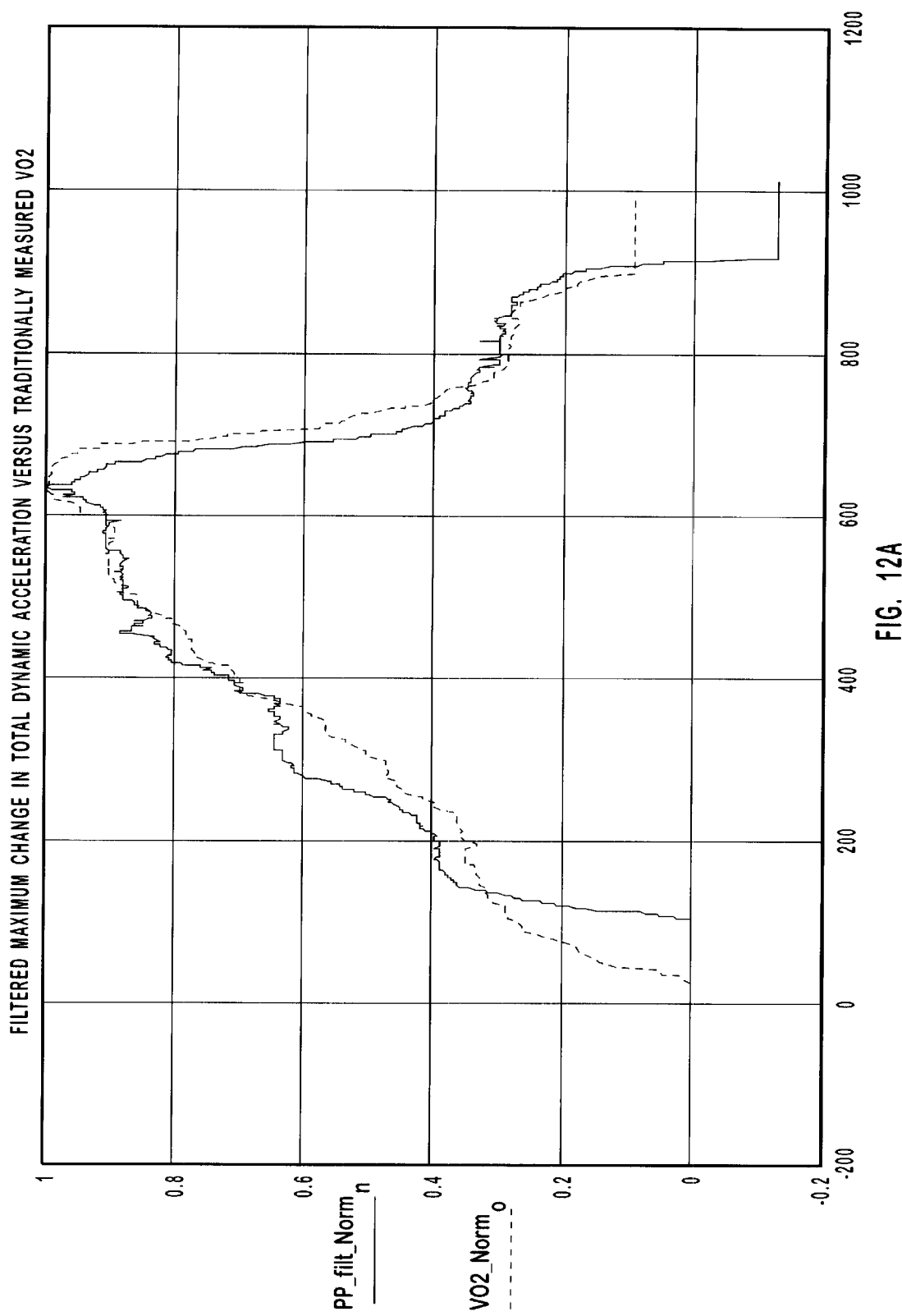
FIG. 12A is a comparison of a plot of the filtered maximum change in total dynamic acceleration over an interval of time with a plot of traditionally measured VO2.
Figure 12B:
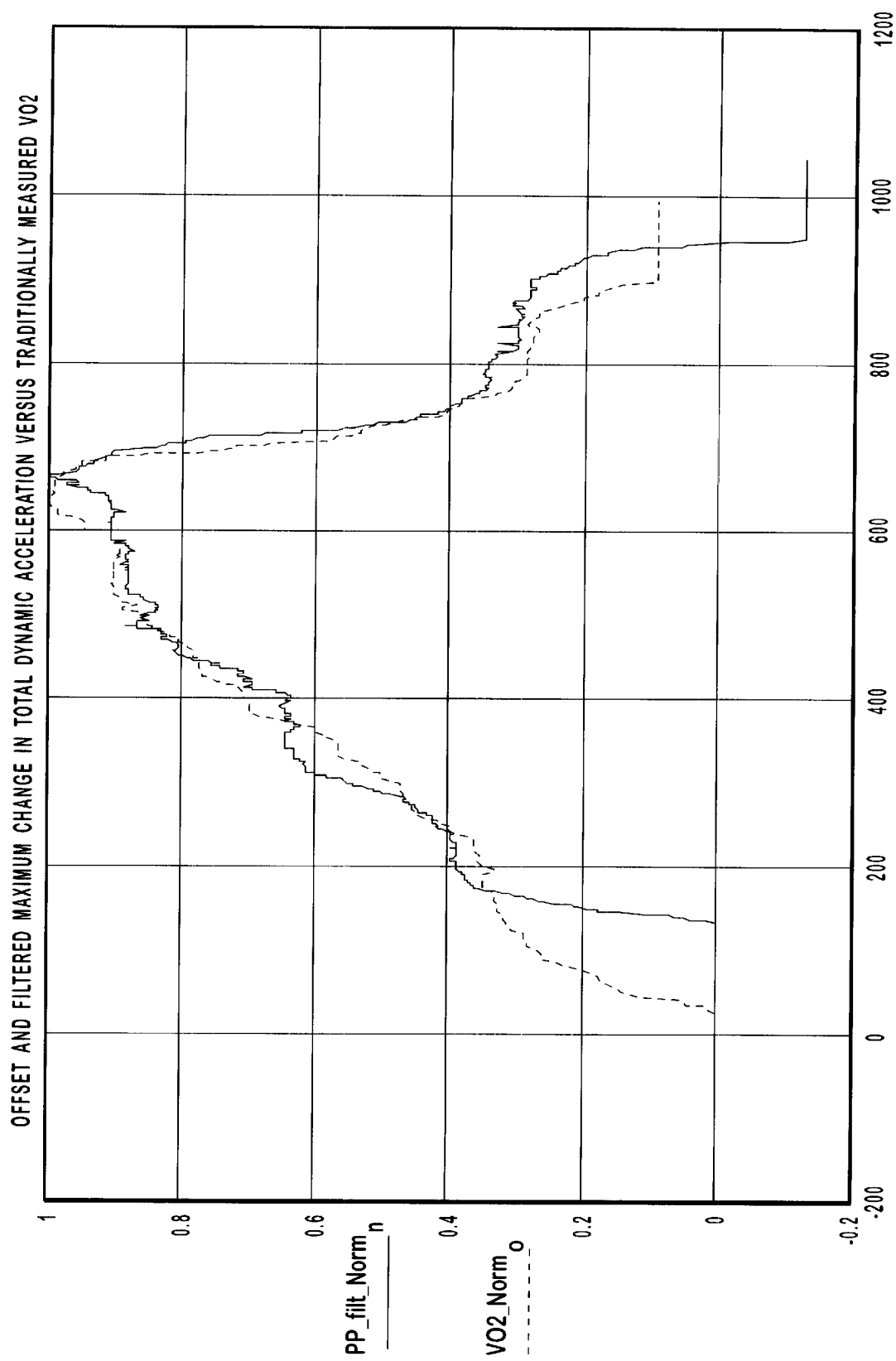
FIG. 12B is a comparison of a plot of the filtered maximum change in total dynamic acceleration having an offset in time with a plot of traditionally measured VO2.

In step 680, the data is graphed with respect to time to generate a graphical representation of the rate of oxygen consumption of the individual. When graphing the information it is important to be sure that all graphs have the same base unit for time. FIG. 12A provides a comparison of a plot of an embodiment of the present invention that has no offset in time with a plot of traditionally measured VO2. FIG. 12B provides a comparison of a plot of an embodiment of the present invention that has an offset in time with a plot of traditionally measured VO2. As provided in FIG. 12B, the offset in time approximately aligns the falling edges of the data sets. In FIGS. 12A and 12B, $PP\_filt\_Norm_n$ represents a determination of an individual's work by employing an embodiment of the present invention and $VO2\_Norm_O$ represents a determination of an individual's work by employing a traditional method.

Therefore, through the utilization of the systems and methods of the present invention, disclosed herein, the rate of oxygen consumption or work of a human body can be determined. Furthermore, VO2 or work can be determined under normal conditions, allowing freedom of movement, and under a variety of types of physical activities. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. A method for determining work performed by a human body by approximating the rate of oxygen consumption, the method comprising the acts of:

monitoring acceleration information of the human body during a period of time;

storing the acceleration information on a local storage device; and using the acceleration information to calculate an approximation of the rate of oxygen consumption of the human body, the calculation comprising the mathematical acts of:

separating the acceleration information, wherein the separation creates a static acceleration component and a dynamic acceleration component;

calculating the magnitude of the dynamic acceleration component; and calculating the maximum change of the dynamic acceleration component; and graphing static acceleration component, dynamic acceleration component, and the maximum change of the dynamic acceleration component with respect to a common time base.

2. A method as recited in claim 1, wherein the act of using the acceleration information to calculate an approximation of the rate of oxygen consumption of the human body further comprises the mathematical act of graphing the maximum change of the dynamic acceleration component with respect to time.

3. A method as recited in claim 1, wherein at least one accelerometer performs the act of monitoring acceleration information.

4. A method as recited in claim 3, wherein the accelerometer measures acceleration relative to at least one axis.

5. A method as recited in claim 3, wherein at least one accelerometer is external to the human body.

6. A method as recited in claim 5, wherein the accelerometer is an element of a patch attached to the human body.

7. A method as recited in claim 1, wherein a monitoring device embedded in the human body performs the act of monitoring acceleration information.

8. A method as recited in claim 1, wherein a central processor performs the act of using the acceleration information to calculate an approximation of the rate of oxygen consumption of the human body.

9. A device for determining an amount of work performed by an individual's body by approximating a rate of oxygen consumption of the body, the method comprising:

means for measuring acceleration information of the human body during a period of time;

means for using the acceleration information to calculate an approximation of the rate of oxygen consumption of the human body, comprising:

means for separating the acceleration information into static and dynamic components means for calculating a magnitude of the dynamic component;

means for calculating a maximum change in the dynamic component;

means for filtering the maximum change; and means for normalizing the filtered maximum change.

10. A device as recited in claim 9, wherein means for measuring acceleration information includes at least one accelerometer.

11. A device as recited in claim 10, wherein the accelerometer is external to the human body.

12. A device as recited in claim 9, wherein the means for measuring acceleration information includes at least one patch adaptable for attachment to the human body.

13. A device as recited in claim 9, wherein the means for measuring acceleration information is adaptable for being embedded in the human body.

14. A device as recited in claim 9, wherein the means for using the acceleration information to calculate an approximation of the rate of oxygen consumption of the human body includes a processor.

15. A device as recited in claim 9, wherein the means for using the acceleration information to calculate an approximation of the rate of oxygen consumption of the human body further includes means for graphing the filtered maximum change with respect to time.

16. A computer program for implementing a method for approximating a rate of oxygen consumption of a human body in order to determine an amount of work performed by the body, the computer program product comprising:

a computer readable medium having computer executable instructions that manipulate acceleration information measured from a human body during a period of time, the instructions when executed are for approximating the rate of oxygen consumption by performing the acts of:

separating the acceleration information into static and dynamic components;

calculating a magnitude for the dynamic component;

calculating a maximum change in the dynamic component; and normalizing the maximum change in the dynamic component.

17. A computer program as recited in claim 16, wherein the acts of separating, calculating, and normalizing are performed by a processor.

* * * * *